(12) United States Patent
Oost et al.

(10) Patent No.: US 8,933,079 B2
(45) Date of Patent: Jan. 13, 2015

(54) PYRIDONE AND PYRIDAZINONE DERIVATIVES AS ANTI-OBESITY AGENTS

(71) Applicants: Thorsten Oost, Biberach an der Riss (DE); Ralf Lotz, Schemmerhofen (DE); Dirk Stenkamp, Biberach an der Riss (DE)

(72) Inventors: Thorsten Oost, Biberach an der Riss (DE); Ralf Lotz, Schemmerhofen (DE); Dirk Stenkamp, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/780,343

(22) Filed: Feb. 28, 2013

(65) Prior Publication Data
US 2013/0237515 A1    Sep. 12, 2013

(30) Foreign Application Priority Data
Mar. 7, 2012    (EP) .................................... 12158464

(51) Int. Cl.
| | |
|---|---|
| A61K 31/501 | (2006.01) |
| A61K 31/4412 | (2006.01) |
| C07D 213/69 | (2006.01) |
| C07D 237/16 | (2006.01) |
| C07D 401/12 | (2006.01) |
| C07D 401/14 | (2006.01) |
| C07D 401/10 | (2006.01) |
| C07D 413/10 | (2006.01) |
| C07D 413/12 | (2006.01) |
| C07D 403/10 | (2006.01) |

(52) U.S. Cl.
CPC ............ *C07D 401/12* (2013.01); *C07D 401/14* (2013.01); *C07D 401/10* (2013.01); *C07D 413/10* (2013.01); *C07D 413/12* (2013.01); *C07D 231/69* (2013.01); *C07D 237/16* (2013.01); *C07D 403/10* (2013.01)
USPC ....... 514/252.01; 514/348; 544/238; 546/296

(58) Field of Classification Search
CPC .. C07D 237/16; C07D 213/69; C07D 401/12; C07D 401/14
USPC .......................................... 544/238; 546/296
See application file for complete search history.

(56) References Cited

U.S. PATENT DOCUMENTS

2013/0237515 A1    9/2013    Oost et al.

FOREIGN PATENT DOCUMENTS

| EP | 1916239 A1 | 4/2008 |
|---|---|---|
| WO | 2008022979 A1 | 2/2008 |
| WO | 2009103478 A1 | 8/2009 |
| WO | 2013131935 A1 | 9/2013 |

OTHER PUBLICATIONS

International Search Report and Written Opinion for PCT/EP2013/054465 mailed Jul. 16, 2013.

*Primary Examiner* — Brian McDowell
(74) *Attorney, Agent, or Firm* — Michael P. Morris; Mary-Ellen M. Devlin

(57) ABSTRACT

Pyridone and pyridazinone derivatives that are active against the melanin-concentrating hormone (MCH) and useful as anti-obesity pharmaceuticals.

11 Claims, No Drawings

PYRIDONE AND PYRIDAZINONE DERIVATIVES AS ANTI-OBESITY AGENTS

FIELD OF THE INVENTION

The present invention relates to new compounds, in particular a compound of the formula I

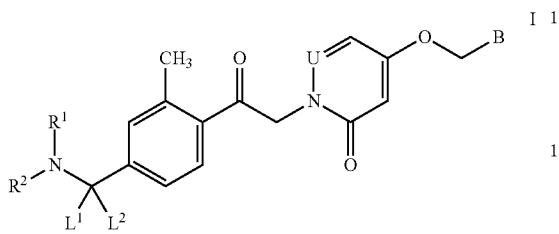

wherein the groups $R^1$, $R^2$, $L^1$, $L^2$, U and B are defined as hereinafter, to processes for preparing such compounds, to pharmaceutical compositions comprising such compounds, to their use as MCH antagonists, and to methods for their therapeutic use, in particular in diseases and conditions mediated by the modulation of the melanin-concentrating hormone (MCH) receptor.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialised countries, have promoted morbid overweight (also known as corpulence or obesity) in recent decades. In affected people, obesity leads directly to restricted mobility and a reduction in the quality of life. There is the additional factor that obesity often leads to other diseases such as, for example, diabetes, dyslipidaemia, high blood pressure, arteriosclerosis and coronary heart disease. Moreover, high body weight alone puts an increased strain on the support and mobility apparatus, which can lead to chronic pain and diseases such as arthritis or osteoarthritis. Thus, obesity is a serious health problem for society.

The term obesity means an excess of adipose tissue in the body. In this connection, obesity is fundamentally to be seen as the increased level of fatness which leads to a health risk. There is no sharp distinction between normal individuals and those suffering from obesity, but the health risk accompanying obesity is presumed to rise continuously as the level of fatness increases.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity. One approach which has been proposed is the therapeutic use of MCH antagonists.

Investigations into the function of MCH in animal models have provided good indications for a role of the peptide in regulating the energy balance, i.e., changing metabolic activity and food intake. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. On the other hand, experiments with MCH knock-out mice are particularly important in showing the function of MCH. Loss of the neuropeptide results in lean animals with a reduced fat mass, which take in significantly less food than control animals.

The anorectic effects of MCH are presumably mediated in rodents through the $G_{\alpha s}$-coupled MCH-1 receptor (MCH-1R), as, unlike primates, ferrets and dogs, no second MCH receptor subtype has hitherto been found in rodents. After losing the MCH-1R, knock-out mice have a lower fat mass, an increased energy conversion and, when fed on a high fat diet, do not put on weight, compared with control animals. Several small-molecule MCH-1R antagonists have been described in the literature which consistently show decreased food intake and body weight reduction in animal models of diet-induced obesity [1].

In addition to its anorectic effect, MCH-1R antagonists also achieve additional anxiolytic and antidepressant effects in behavioural experiments [1]. Thus, there are clear indications that the MCH-MCH-1R system is involved not only in regulating the energy balance but also in affectivity.

LITERATURE

1. Chung, S. et al., *Recent Updates on the Melanin-Concentrating Hormone (MCH) and its Receptor System: Lessons from MCH1R Antagonists*. J Mol Neurosci, 2011. 43: p. 115-121

In the patent literature (WO 2008/022979) pyridone and pyridazinone derivatives of the formula I

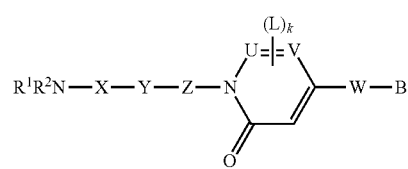

are described as MCH antagonists. In case the group Y denotes phenyl a substitution with methyl in ortho position is not described therein.

In the patent literature (WO 2009/103478) specific pyridone and pyridazinone derivatives are described as MCH antagonists.

In the patent literature (EP 1916239) pyridone derivatives of the formula

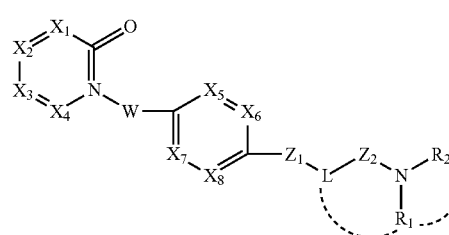

are described as MCH antagonists.

Aim of the Present Invention

The aim of the present invention is to provide new compounds, in particular new pyridone and pyridazinone derivatives, which are active against the MCH receptor, in particular against the MCH receptor 1 (MCH-1R).

Another aim of the present invention is to provide new compounds, in particular new pyridone and pyridazinone derivatives, which are antagonists of the MCH-1R.

A further aim of the present invention is to provide new compounds, in particular pyridone and pyridazinone derivatives, which have a greater metabolic stability than pyridone and pyridazinone derivatives of the prior art.

A further aim of the present invention is to provide new compounds, in particular pyridone and pyridazinone derivatives, which are MCH-1R antagonists with suitable pharmacological and pharmacokinetic properties to use them as medicaments.

A further aim of the present invention is to provide methods for treating a disease or condition mediated by the MCH receptor in a patient.

A further aim of the present invention is to provide a pharmaceutical composition comprising at least one compound according to the invention.

A further aim of the present invention is to provide methods for the synthesis of the new compounds, in particular pyridone and pyridazinone derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

Object of the Invention

It has now been found that the compounds according to the invention described in more detail hereinafter have surprising and particularly advantageous properties, and in particular as MCH-1R antagonists. Furthermore the compounds according to the invention have a good metabolic stability. It has been found that compounds according to this invention with a methyl substituent at the ortho-position (with respect to the carbonyl group) at the central phenyl ring have an improved metabolic stability compared with corresponding known compounds without such a methyl substituent.

In a first aspect the invention thus relates to a compound of formula I wherein
$R^1$, $R^2$ independently of each other are selected from the group $R^1$-G1 consisting of H, $C_{1-6}$-alkyl and $C_{3-7}$-cycloalkyl, while the alkyl or cycloalkyl group may be mono- or polysubstituted by identical or different groups $R^{11}$, and a —$CH_2$— group in position 3 or 4 of a 5-, 6- or 7-membered cycloalkyl group may be replaced by —O—, —S—, —S(=O)—, —S(=O)$_2$— or —$NR^{12}$—; or $R^1$ and $R^2$ are linked to each other and together form a group which is selected from the group $R^1$—$R^2$-G1 consisting of a $C_{3-6}$-alkylene bridge, wherein a —$CH_2$— group not adjacent to the N atom of the $R^1R^2N$— group may be replaced by —O—, —S—, —S(=O)—, —S(=O)$_2$— or —$NR^{12}$—, and wherein one or more H atoms of the alkylene bridge may be replaced by identical or different groups $R^{11}$; or $R^1$ and $R^2$ are linked to each other such that the $R^1R^2N$— group forms a bridged cyclic ring system with 5 to 8 C-atoms wherein one or more H atoms of the bridged cyclic ring system may be replaced by identical or different groups $R^{11}$, and $L^1$, $L^2$ independently of each other are selected from the group $L^1$-G1 consisting of H and $C_{1-3}$-alkyl, or $L^1$ and $L^2$ are linked to each other and together form a group which is selected from the group $L^1$-$L^2$-G1 consisting of a $C_{2-5}$-alkylene bridge; and U is selected from the group U-G1 consisting of CH and N; and B is selected from the group B-G1 consisting of phenyl and pyridinyl each of which may be mono- or polysubstituted by identical or different substituents $R^{20}$; and $R^{11}$ is selected from the group $R^{11}$-G1 consisting of OH, F, Cl, Br, CN, $C_{1-6}$-alkyl, $C_{3-6}$-cycloalkyl, $C_{1-4}$-alkyl-O— and $R^{13}R^{14}N$—, while each of the above mentioned alkyl or cycloalkyl groups may be substituted independently of one another by one or more substituents selected from F, Cl, Br, OH, CN, CF$_3$, $C_{1-3}$-alkyl, $C_{1-3}$-alkyl-O— and HO—$C_{1-3}$-alkyl; and $R^{12}$ is selected from the group $R^{12}$-G1 consisting of H, $C_{1-4}$-alkyl and $C_{1-4}$-alkyl-C(=O)—; and $R^{13}$, $R^{14}$ independently of each other are selected from the group $R^{13}$-G1 consisting of H and $C_{1-4}$-alkyl; and $R^{20}$ is selected from the group $R^{20}$-G1 consisting of F, Cl, Br, OH, CN, NO$_2$, $C_{1-4}$-alkyl and $C_{1-4}$-alkyl-O—, wherein each alkyl group may be substituted with one or more substituents independently of each other selected from F, Cl, Br, OH, CN, NO$_2$ and $C_{1-4}$-alkyl-O—; and while, unless otherwise stated, the above-mentioned alkyl groups may be straight-chain or branched, including any tautomers and stereoisomers thereof, or a salt thereof or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more excipients.

In a further aspect this invention relates to a method for treating a disease or condition which is mediated by modulating the activity of the MCH receptor in a patient in need thereof characterized in that a compound of general formula I or a pharmaceutically acceptable salt thereof is administered to the patient.

According to another aspect of the invention, there is provided a method for treating a disease or condition which is mediated by blocking the MCH receptor in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, $R^{11}$, $R^{12}$, $R^{13}$, $R^{14}$, $R^{20}$, $L^1$, $L^2$, U and B are defined as above and hereinafter. If residues, substituents, or groups occur several times in a compound, as for example $R^{11}$ or $R^{20}$, they may have the same or different meanings. Some preferred meanings of individual groups and substituents of the compounds according to the invention will be given hereinafter. Any and each of these definitions may be combined with each other.

$R^1$, $R^2$:

$R^1$-G1:

The groups $R^1$ and $R^2$ are independently of each other preferably selected from the group $R^1$-G1 as defined hereinbefore and hereinafter. In case $R^1$ denotes H, then $R^2$ preferably has a meaning different than H.

Examples of the group $R^1R^2N$— wherein $R^1$ and $R^2$ are linked to each other such that the $R^1R^2N$— group forms a bridged cyclic ring system with 5 to 8 C-atoms, in particular 6 or 7 C-atoms are:

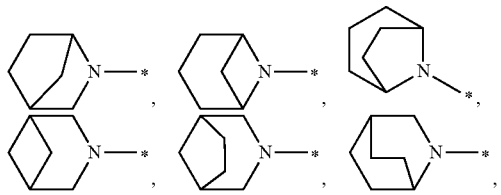

In each of the above bridged cyclic ring systems one or more, in particular one or two, H atoms may be replaced by identical or different groups $R^{11}$.

$R^1$-G2:

According to one embodiment the groups $R^1$ and $R^2$ independently of each other are selected from the group $R^1$-G2 consisting of H, $C_{1-4}$-alkyl and $C_{3-6}$-cycloalkyl, while the alkyl or cycloalkyl group may be mono- or polysubstituted by identical or different groups $R^{11}$, and a —$CH_2$— group in position 3 or 4 of a 5- or 6-membered cycloalkyl group may be replaced by —O— or —$NR^{12}$—. In case $R^1$ denotes H, then $R^2$ preferably has a meaning different than H.

$R^1$-G3:

According to one embodiment the groups $R^1$ and $R^2$ independently of each other are selected from the group $R^1$-G3 consisting of H and $C_{1-4}$-alkyl, while the alkyl group may be mono- or polysubstituted by identical or different groups $R^{11}$.

Preferred examples of the group $R^1$-G3 are H, methyl, ethyl, n-propyl and i-propyl.

In case $R^1$ denotes H, then $R^2$ preferably has a meaning different than H.

$R^1$-$R^2$-G1:

According to another embodiment the groups $R^1$ and $R^2$ are linked to each other and together form a group which is selected from the group $R^1$-$R^2$-G1 as defined hereinbefore and hereinafter or $R^1$ and $R^2$ are linked to each other such that the $R^1R^2N$— group forms a bridged cyclic ring system with 5 to 8 C-atoms wherein one or more H atoms of the bridged cyclic ring system may be replaced by identical or different groups $R^{11}$.

$R^1$-$R^2$-G2:

According to another embodiment the groups $R^1$ and $R^2$ are linked to each other and together form a group which is selected from the group $R^1$-$R^2$-G2 consisting of a $C_{3-5}$-alkylene bridge, wherein a —$CH_2$— group not adjacent to the N atom of the $R^1R^2N$— group may be replaced by —O— or —$NR^{12}$—, and wherein 1 or 2H atoms of the alkylene bridge may be replaced by identical or different groups $R^{11}$, or $R^1$ and $R^2$ are linked to each other such that the $R^1R^2N$— group forms a bridged cyclic ring system with 5, 6 or 7 C-atoms wherein one or more, in particular one or two, H atoms of the bridged cyclic ring system may be replaced by identical or different groups $R^{11}$.

$R^1$-$R^2$-G3:

According to another embodiment the groups $R^1$ and $R^2$ are linked to each other such that the group

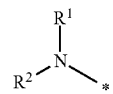

is selected from the group $R^1$-$R^2$-G3 consisting of the cyclic groups

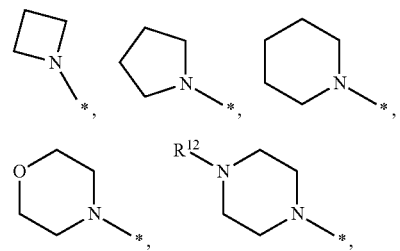

or $R^1$ and $R^2$ are linked to each other such that the $R^1R^2N$— group forms the bridged cyclic ring system

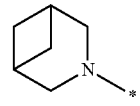

wherein in each cyclic group or in the bridged cyclic ring system one or more, in particular one or two, H atoms may be replaced by identical or different groups $R^{11}$.

Preferred examples according to this embodiment are

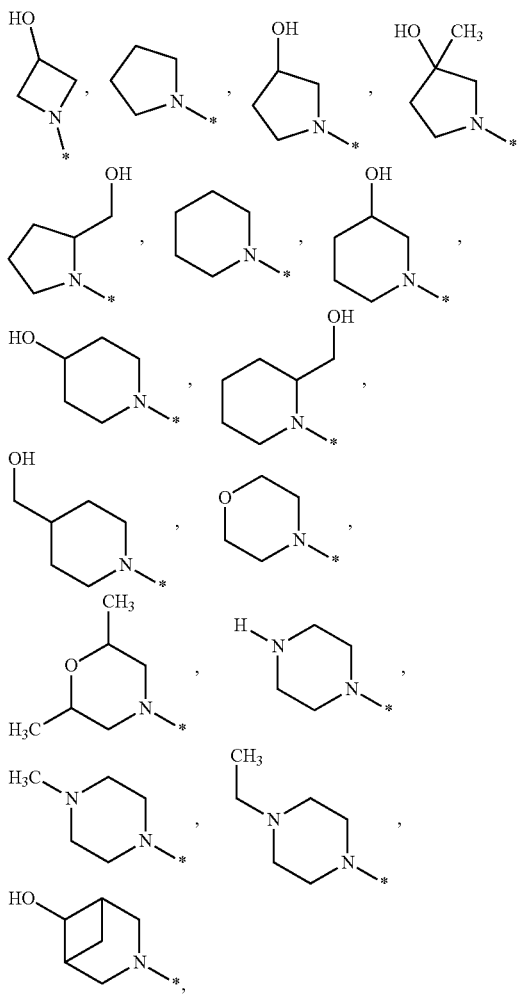

wherein each cyclic group may be substituted with an additional —CH$_3$ group.

$L^1$, $L^2$:

$L^1$-G1:
The groups $L^1$ and $L^2$ are independently of each other preferably selected from the group $L^1$-G1 as defined hereinbefore and hereinafter.

$L^1$-G2:
According to one embodiment the groups $L^1$ and $L^2$ are independently of each other selected from the group $L^1$-G2 consisting of H and CH$_3$.

According to a preferred example $L^1$ and $L^2$ denote H.

According to another preferred example $L^1$ denotes H and $L^2$ denotes CH$_3$.

U:

U-G1:
The group U is preferably selected from the group U-G1 as defined hereinbefore and hereinafter.

U-G2:
According to one embodiment the group U is selected from the group U-G2 consisting of CH.

U-G3:
According to another embodiment the group U is selected from the group U-G3 consisting of N.

B:

B-G1:
The group B is preferably selected from the group B-G1 as defined hereinbefore and hereinafter.

B-G2:
According to one embodiment the group B is selected from the group B-G2 consisting of phenyl which may be substituted by 1, 2 or 3 identical or different substituents $R^{20}$.

B-G3:
According to another embodiment the group B is selected from the group B-G3 consisting of pyridinyl which may be substituted by 1, 2 or 3 identical or different substituents $R^{20}$.

$R^{11}$:

$R^{11}$-G1:
The group $R^{11}$ is preferably selected from the group $R^{11}$-G1 as defined hereinbefore and hereinafter.

$R^{11}$-G2:
According to one embodiment the group $R^{11}$ is selected from the group $R^{11}$-G2 consisting of OH, F, $C_{1-4}$-alkyl, $C_{1-3}$-alkyl-O—, $C_{3-6}$-cycloalkyl and $C_{3-6}$-cycloalkyl-O—, while each of the above mentioned alkyl and cycloalkyl groups may be substituted by one or more substituents independently of each other selected from F, OH and $C_{1-3}$-alkyl-O—.

$R^{11}$-G3:
According to one embodiment the group $R^{11}$ is selected from the group $R^{11}$-G3 consisting of OH and $C_{1-3}$-alkyl, wherein alkyl may be substituted by OH.

Preferred examples of the group $R^{11}$-G3 are OH, CH$_3$ and HO—CH$_2$—, $R^{12}$:

$R^{12}$-G1:
The group $R^{12}$ is preferably selected from the group $R^{12}$-G1 as defined hereinbefore and hereinafter.

$R^{12}$-G2:
According to one embodiment the group $R^{12}$ is selected from the group $R^{12}$-G2 consisting of H and $C_{1-3}$-alkyl.

Preferred examples of the group $R^{12}$-G2 are H, CH$_3$ and H$_3$C—CH$_2$—, $R^{13}$:

$R^{13}$-G1:
The groups $R^{13}$ and $R^{14}$ are independently of each other preferably selected from the group $R^{13}$-G1 as defined hereinbefore and hereinafter.

$R^{13}$-G2:
According to one embodiment the groups $R^{13}$ and $R^{14}$ are independently of each other selected from the group $R^{14}$-G2 consisting of H and CH$_3$.

$R^{20}$:

$R^{20}$-G1:
The group $R^{20}$ is preferably selected from the group $R^{20}$-G1 as defined hereinbefore and hereinafter.

$R^{20}$-G2:
According to one embodiment the group $R^{20}$ is selected from the group $R^{20}$-G2 consisting of F, Cl, Br, OH, CN, $C_{1-4}$-alkyl and $C_{1-4}$-alkyl-O—, wherein each alkyl group may be substituted with one or more substituents independently of each other selected from F, OH, CN and $C_{1-4}$-alkyl-O—.

Preferred examples of the group $R^{20}$-G3 are F, Cl, Br, H$_3$C—O—.

The following preferred embodiments of compounds of the formula I are described using generic formulae I.1 and I.2 wherein any tautomers and stereoisomers, solvates and hydrates thereof, and salts thereof, in particular the pharmaceutically acceptable salts thereof, are encompassed.

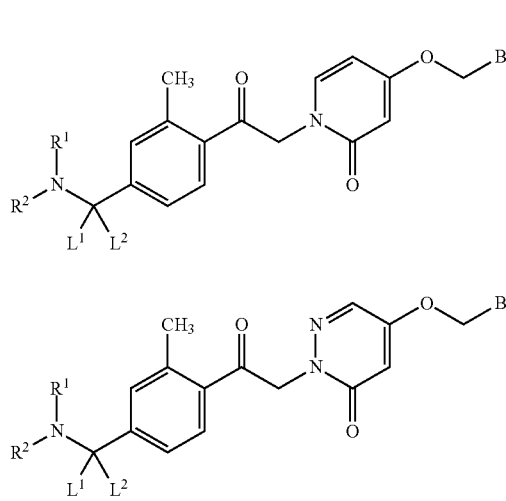

wherein the groups $R^1$, $R^2$, $L^1$, $L^2$ and B are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents are defined according to the definitions set forth hereinbefore:

| Embodiment | Formula | $R^1$, R2 | $L^1$, L2 | B |
| --- | --- | --- | --- | --- |
| E-1 | I.1 | $R^1$-G1 | $L^1$-G1 | B-G1 |
| E-2 | I.1 | $R^1$-G2 | $L^1$-G1 | B-G1 |
| E-3 | I.1 | $R^1$-G3 | $L^1$-G2 | B-G2 |
| E-4 | I.1 | $R^1$-G3 | $L^1$-G2 | B-G3 |
| E-5 | I.1 | $R^1$-$R^2$-G1 | $L^1$-G1 | B-G1 |
| E-6 | I.1 | $R^1$-$R^2$-G2 | $L^1$-G1 | B-G1 |
| E-7 | I.1 | $R^1$-$R^2$-G3 | $L^1$-G2 | B-G2 |
| E-8 | I.1 | $R^1$-$R^2$-G3 | $L^1$-G2 | B-G3 |
| E-9 | I.2 | $R^1$-G1 | $L^1$-G1 | B-G1 |
| E-10 | I.2 | $R^1$-G2 | $L^1$-G1 | B-G1 |
| E-11 | I.2 | $R^1$-G3 | $L^1$-G2 | B-G2 |
| E-12 | I.2 | $R^1$-G3 | $L^1$-G2 | B-G3 |
| E-13 | I.2 | $R^1$-$R^2$-G1 | $L^1$-G1 | B-G1 |
| E-14 | I.2 | $R^1$-$R^2$-G2 | $L^1$-G1 | B-G1 |
| E-15 | I.2 | $R^1$-$R^2$-G3 | $L^1$-G2 | B-G2 |
| E-16 | I.2 | $R^1$-$R^2$-G3 | $L^1$-G2 | B-G3 |

The following particularly preferred embodiments of compounds of the formula I are described using generic formulae I.1.1, I.1.2, I.2.1 and I.2.2 wherein any tautomers and stereoisomers, solvates and hydrates thereof, and salts thereof, in particular the pharmaceutically acceptable salts thereof, are encompassed.

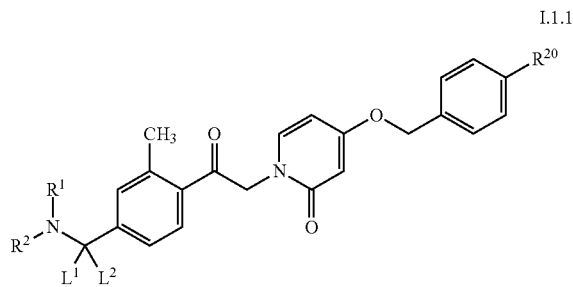

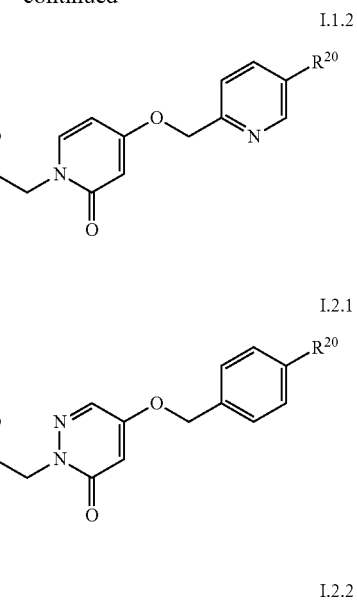

Examples of preferred subgeneric embodiments according to the present invention are set forth in the following table, wherein each substituent group of each embodiment is defined according to the definitions set forth hereinbefore and wherein all other substituents are defined according to the definitions set forth hereinbefore:

| Embodiment | Formula | $R^1$, R2 | $L^1$, L2 | $R^{20}$ |
| --- | --- | --- | --- | --- |
| E-17 | I.1.1 | $R^1$-G1 or $R^1$-$R^2$-G1 | $L^1$-G1 | $R^{20}$-G1 |
| E-18 | I.1.1 | $R^1$-G2 or $R^1$-$R^2$-G2 | $L^1$-G1 | $R^{20}$-G1 |
| E-19 | I.1.1 | $R^1$-G3 or $R^1$-$R^2$-G3 | $L^1$-G2 | $R^{20}$-G2 |
| E-20 | I.1.2 | $R^1$-G1 or $R^1$-$R^2$-G1 | $L^1$-G1 | $R^{20}$-G1 |
| E-21 | I.1.2 | $R^1$-G2 or $R^1$-$R^2$-G2 | $L^1$-G1 | $R^{20}$-G1 |
| E-22 | I.1.2 | $R^1$-G3 or $R^1$-$R^2$-G3 | $L^1$-G2 | $R^{20}$-G2 |
| E-23 | I.2.1 | $R^1$-G1 or $R^1$-$R^2$-G1 | $L^1$-G1 | $R^{20}$-G1 |
| E-24 | I.2.1 | $R^1$-G2 or $R^1$-$R^2$-G2 | $L^1$-G1 | $R^{20}$-G1 |
| E-25 | I.2.1 | $R^1$-G3 or $R^1$-$R^2$-G3 | $L^1$-G2 | $R^{20}$-G2 |

-continued

| Embodiment | Formula | R¹, R2 | L¹, L2 | $R^{20}$ |
|---|---|---|---|---|
| E-26 | I.2.2 | R¹-G1 or R¹-R²-G1 | L¹-G1 | $R^{20}$-G1 |
| E-27 | I.2.2 | R¹-G2 or R¹-R²-G2 | L¹-G1 | $R^{20}$-G1 |
| E-28 | I.2.2 | R¹-G3 or R¹-R²-G3 | L¹-G2 | $R^{20}$-G2 |

Particularly preferred compounds, including their tautomers and stereoisomers, the salts thereof, or any solvates or hydrates thereof, are described in the experimental section hereinafter.

The following compounds are mentioned as examples of compounds according to the invention:

| Example | Name |
|---|---|
| 1.1 | 4-Benzyloxy-1-{2-[4-(3-hydroxy-azetidin-1-ylmethyl)-2-methyl-phenyl]-2-oxo-ethyl}-1H-pyridin-2-one |
| 1.2 | 4-Benzyloxy-1-[2-(2-methyl-4-methylaminomethyl-phenyl)-2-oxo-ethyl]-1H-pyridin-2-one |
| 1.3 | 4-Benzyloxy-1-{2-[4-(4-hydroxy-piperidin-1-ylmethyl)-2-methyl-phenyl]-2-oxo-ethyl}-1H-pyridin-2-one |
| 1.5 | 4-Benzyloxy-1-{2-[2-methyl-4-(4-methyl-piperazin-1-ylmethyl)-phenyl]-2-oxo-ethyl}-1H-pyridin-2-one |
| 1.6 | 4-Benzyloxy-1-{2-[4-(4-hydroxymethyl-piperidin-1-ylmethyl)-2-methyl-phenyl]-2-oxo-ethyl}-1H-pyridin-2-one |
| 1.7 | 4-Benzyloxy-1-[2-(2-methyl-4-pyrrolidin-1-ylmethyl-phenyl)-2-oxo-ethyl]-1H-pyridin-2-one |
| 1.8 | 4-Benzyloxy-1-[2-(4-dimethylaminomethyl-2-methyl-phenyl)-2-oxo-ethyl]-1H-pyridin-2-one |
| 1.11 | (S)-4-Benzyloxy-1-{2-[4-(3-hydroxy-pyrrolidin-1-ylmethyl)-2-methyl-phenyl]-2-oxo-ethyl}-1H-pyridin-2-one |
| 1.12 | 4-Benzyloxy-1-[2-(4-ethylaminomethyl-2-methyl-phenyl)-2-oxo-ethyl]-1H-pyridin-2-one |
| 1.13 | (S)-4-Benzyloxy-1-{2-[4-(3-hydroxy-piperidin-1-ylmethyl)-2-methyl-phenyl]-2-oxo-ethyl}-1H-pyridin-2-one |
| 1.15 | (R)-4-Benzyloxy-1-{2-[4-(3-hydroxy-piperidin-1-ylmethyl)-2-methyl-phenyl]-2-oxo-ethyl}-1H-pyridin-2-one |
| 1.17 | (S)-4-Benzyloxy-1-{2-[4-(2-hydroxymethyl-pyrrolidin-1-ylmethyl)-2-methyl-phenyl]-2-oxo-ethyl}-1H-pyridin-2-one |
| 3.2 | 4-(5-Chloro-pyridin-2-ylmethoxy)-1-{2-[4-((S)-2-hydroxymethyl-pyrrolidin-1-ylmethyl)-2-methyl-phenyl]-2-oxo-ethyl}-1H-pyridin-2-one |
| 3.4 | (R)-4-(5-Chloro-pyridin-2-ylmethoxy)-1-{2-[4-(3-hydroxy-pyrrolidin-1-ylmethyl)-2-methyl-phenyl]-2-oxo-ethyl}-1H-pyridin-2-one |
| 3.8 | 4-(5-Chloro-pyridin-2-ylmethoxy)-1-[2-(2-methyl-4-pyrrolidin-1-ylmethyl-phenyl)-2-oxo-ethyl]-1H-pyridin-2-one |
| 3.9 | 4-(5-Chloro-pyridin-2-ylmethoxy)-1-[2-(4-dimethylaminomethyl-2-methyl-phenyl)-2-oxo-ethyl]-1H-pyridin-2-one |
| 3.11 | 4-(5-Chloro-pyridin-2-ylmethoxy)-1-[2-(4-ethylaminomethyl-2-methyl-phenyl)-2-oxo-ethyl]-1H-pyridin-2-one |
| 3.13 | (R)-4-(5-Chloro-pyridin-2-ylmethoxy)-1-{2-[4-(3-hydroxy-piperidin-1-ylmethyl)-2-methyl-pheny]-2-oxo-ethyl}-1H-pyridin-2-one |
| 3.15 | 4-(5-Chloro-pyridin-2-ylmethoxy)-1-{2-[4-(3-hydroxy-azetidin-1-ylmethyl)-2-methyl-phenyl]-2-oxo-ethyl}-1H-pyridin-2-one |
| 4.1 | 4-(5-Bromo-pyridin-2-ylmethoxy)-1-[2-(4-dimethylaminomethyl-2-methyl-phenyl)-2-oxo-ethyl]-1H-pyridin-2-one |
| 4.2 | 4-(5-Bromo-pyridin-2-ylmethoxy)-1-{2-[4-(4-hydroxy-piperidin-1-ylmethyl)-2-methyl-phenyl]-2-oxo-ethyl}-1H-pyridin-2-one |
| 4.3 | 4-(5-Bromo-pyridin-2-ylmethoxy)-1-{2-[4-(4-hydroxymethyl-piperidin-1-ylmethyl)-2-methyl-phenyl]-2-oxo-ethyl}-1H-pyridin-2-one |
| 4.4 | (S)-4-(5-Bromo-pyridin-2-ylmethoxy)-1-{2-[4-(3-hydroxy-piperidin-1-ylmethyl)-2-methyl-phenyl]-2-oxo-ethyl}-1H-pyridin-2-one |
| 4.5 | (S)-4-(5-Bromo-pyridin-2-ylmethoxy)-1-{2-[4-(2-hydroxymethyl-pyrrolidin-1-ylmethyl)-2-methyl-phenyl]-2-oxo-ethyl}-1H-pyridin-2-one |
| 4.6 | 4-(5-Bromo-pyridin-2-ylmethoxy)-1-[2-(4-ethylaminomethyl-2-methyl-phenyl)-2-oxo-ethyl]-1H-pyridin-2-one |
| 4.8 | 4-(5-Bromo-pyridin-2-ylmethoxy)-1-[2-(2-methyl-4-pyrrolidin-1-ylmethyl-phenyl)-2-oxo-ethyl]-1H-pyridin-2-one |
| 4.9 | (R)-4-(5-Bromo-pyridin-2-ylmethoxy)-1-{2-[4-(3-hydroxy-pyrrolidin-1-ylmethyl)-2-methyl-phenyl]-2-oxo-ethyl}-1H-pyridin-2-one |
| 4.12 | (R)-4-(5-Bromo-pyridin-2-ylmethoxy)-1-{2-[4-(3-hydroxy-piperidin-1-ylmethyl)-2-methyl-phenyl]-2-oxo-ethyl}-1H-pyridin-2-one |
| 4.13 | 4-(5-Bromo-pyridin-2-ylmethoxy)-1-[2-(2-methyl-4-methylaminomethyl-phenyl)-2-oxo-ethyl]-1H-pyridin-2-one |
| 4.15 | 4-(5-Bromo-pyridin-2-ylmethoxy)-1-{2-[4-(isopropylamino-methyl)-2-methyl-phenyl]-2-oxo-ethyl}-1H-pyridin-2-one |
| 4.17 | 4-(5-Bromo-pyridin-2-ylmethoxy)-1-(2-{4-[(isopropyl-methyl-amino)-methyl]-2-methyl-phenyl}-2-oxo-ethyl)-1H-pyridin-2-one |
| 4.18 | 4-(5-Bromo-pyridin-2-ylmethoxy)-1-(2-{4-[(ethyl-methyl-amino)-methyl]-2-methyl-phenyl}-2-oxo-ethyl)-1H-pyridin-2-one |
| 4.20 | 4-(5-Bromo-pyridin-2-ylmethoxy)-1-[2-(4-diethylaminomethyl-2-methyl-phenyl)-2-oxo-ethyl]-1H-pyridin-2-one |
| 4.21 | 1-[2-(4-Azetidin-1-ylmethyl-2-methyl-phenyl)-2-oxo-ethyl]-4-(5-bromo-pyridin-2-ylmethoxy)-1H-pyridin-2-one |
| 5.2 | 5-Benzyloxy-2-[2-(4-dimethylaminomethyl-2-methyl-phenyl)-2-oxo-ethyl]-2H-pyridazin-3-one |
| 5.3 | (S)-5-Benzyloxy-2-{2-[4-(2-hydroxymethyl-pyrrolidin-1-ylmethyl)-2-methyl-phenyl]-2-oxo-ethyl}-2H-pyridazin-3-one |
| 5.4 | (R)-5-Benzyloxy-2-{2-[4-(3-hydroxy-pyrrolidin-1-ylmethyl)-2-methyl-phenyl]-2-oxo-ethyl}-2H-pyridazin-3-one |
| 5.6 | 5-Benzyloxy-2-[2-(4-ethylaminomethyl-2-methyl-phenyl)-2-oxo-ethyl]-2H-pyridazin-3-one |
| 5.7 | 5-Benzyloxy-2-{2-[4-(3-hydroxy-azetidin-1-ylmethyl)-2-methyl-phenyl]-2-oxo-ethyl}-2H-pyridazin-3-one |
| 5.9 | 5-Benzyloxy-2-{2-[2-methyl-4-(2-methyl-morpholin-4-ylmethyl)-phenyl]-2-oxo-ethyl}-2H-pyridazin-3-one |
| 5.11 | 5-Benzyloxy-2-{2-[4-(4-hydroxymethyl-piperidin-1-ylmethyl)-2-methyl-phenyl]-2-oxo-ethyl}-2H-pyridazin-3-one |
| 5.12 | (R)-5-Benzyloxy-2-{2-[4-(2-hydroxymethyl-piperidin-1-ylmethyl)-2-methyl-phenyl]-2-oxo-ethyl}-2H-pyridazin-3-one |
| 5.13 | (S)-5-Benzyloxy-2-{2-[4-(3-hydroxy-piperidin-1-ylmethyl)-2-methyl-phenyl]-2-oxo-ethyl}-2H-pyridazin-3-one |
| 5.14 | 5-Benzyloxy-2-{2-[4-(3-hydroxy-3-methyl-pyrrolidin-1-ylmethyl)-2-methyl-phenyl]-2-oxo-ethyl}-2H-pyridazin-3-one |
| 6.1 | 5-(5-Fluoro-pyridin-2-ylmethoxy)-2-[2-(2-methyl-4-pyrrolidin-1-ylmethyl-phenyl)-2-oxo-ethyl]-2H-pyridazin-3-one |
| 6.2 | 5-(5-Fluoro-pyridin-2-ylmethoxy)-2-[2-(2-methyl-4-piperidin-1-ylmethyl-phenyl)-2-oxo-ethyl]-2H-pyridazin-3-one |
| 7.1 | (S)-5-(5-Chloro-pyridin-2-ylmethoxy)-2-{2-[4-(2-hydroxymethyl-pyrrolidin-1-ylmethyl)-2-methyl-phenyl]-2-oxo-ethyl}-2H-pyridazin-3-one |
| 7.6 | 5-(5-Chloro-pyridin-2-ylmethoxy)-2-[2-(2-methyl-4-methylaminomethyl-phenyl)-2-oxo-ethyl]-2H-pyridazin-3-one |
| 7.7 | 5-(5-Chloro-pyridin-2-ylmethoxy)-2-[2-(4-ethylaminomethyl-2-methyl-phenyl)-2-oxo-ethyl]-2H-pyridazin-3-one |
| 7.13 | (R)-5-(5-Chloro-pyridin-2-ylmethoxy)-2-{2-[4-(2-hydroxymethyl-piperidin-1-ylmethyl)-2-methyl-phenyl]-2-oxo-ethyl}-2H-pyridazin-3-one |
| 7.14 | 5-(5-Chloro-pyridin-2-ylmethoxy)-2-{2-[4-(4-hydroxy-piperidin-1-ylmethyl)-2-methyl-phenyl]-2-oxo-ethyl}-2H-pyridazin-3-one |
| 7.15 | 5-(5-Chloro-pyridin-2-ylmethoxy)-2-[2-(2-methyl-4-pyrrolidin-1-ylmethyl-phenyl)-2-oxo-ethyl]-2H-pyridazin-3-one |
| 7.16 | 5-(5-Chloro-pyridin-2-ylmethoxy)-2-[2-(4-dimethylaminomethyl-2-methyl-phenyl)-2-oxo-ethyl]-2H-pyridazin-3-one |
| 8.2 | 5-(5-Bromo-pyridin-2-ylmethoxy)-2-{2-[4-(3-hydroxy-azetidin-1-ylmethyl)-2-methyl-phenyl]-2-oxo-ethyl}-2H-pyridazin-3-one |
| 8.3 | 5-(5-Bromo-pyridin-2-ylmethoxy)-2-[2-(4-dimethylaminomethyl-2-methyl-phenyl)-2-oxo-ethyl]-2H-pyridazin-3-one |
| 8.6 | (R)-5-(5-Bromo-pyridin-2-ylmethoxy)-2-{2-[4-(3-hydroxy-piperidin-1-ylmethyl)-2-methyl-phenyl]-2-oxo-ethyl}-2H-pyridazin-3-one |

-continued

| Example | Name |
|---|---|
| 8.7 | (R)-5-(5-Bromo-pyridin-2-ylmethoxy)-2-{2-[4-(2-hydroxymethyl-piperidin-1-ylmethyl)-2-methyl-phenyl]-2-oxo-ethyl}-2H-pyridazin-3-one |
| 8.8 | 5-(5-Bromo-pyridin-2-ylmethoxy)-2-[2-(4-ethylaminomethyl-2-methyl-phenyl)-2-oxo-ethyl]-2H-pyridazin-3-one |
| 8.9 | 5-(5-Bromo-pyridin-2-ylmethoxy)-2-{2-[4-(4-hydroxy-piperidin-1-ylmethyl)-2-methyl-phenyl]-2-oxo-ethyl}-2H-pyridazin-3-one |
| 8.10 | 5-(5-Bromo-pyridin-2-ylmethoxy)-2-[2-(2-methyl-4-methylaminomethyl-phenyl)-2-oxo-ethyl]-2H-pyridazin-3-one | more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

Scheme 1:

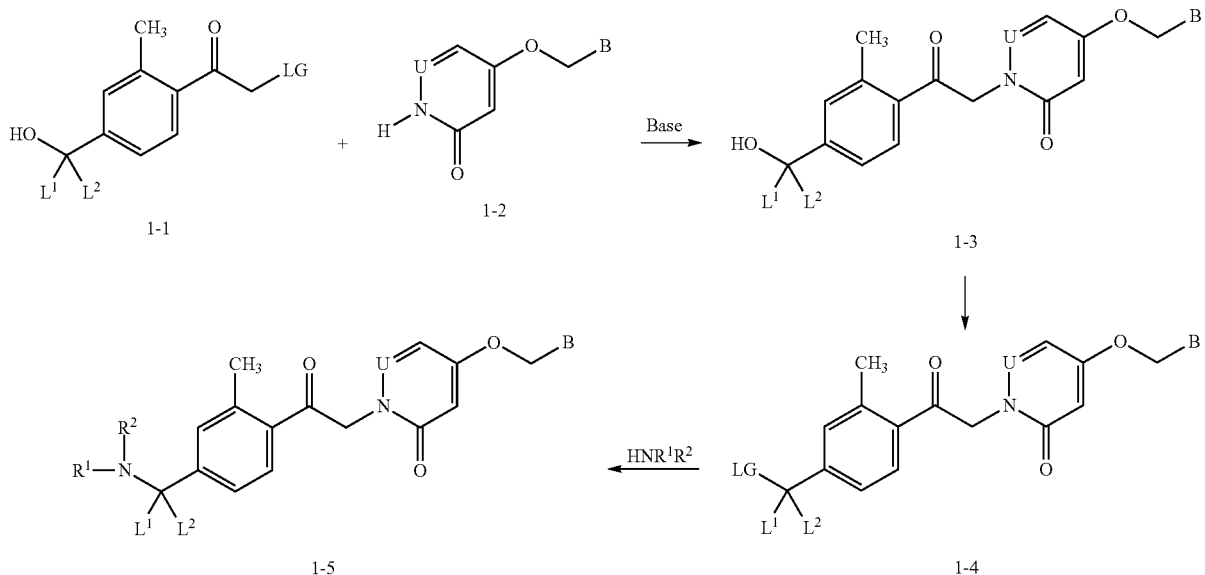

-continued

| Example | Name |
|---|---|
| 9.1 | 2-[2-(4-Dimethylaminomethyl-2-methyl-phenyl)-2-oxo-ethyl]-5-(5-methoxy-pyridin-2-ylmethoxy)-2H-pyridazin-3-one |
| 9.2 | 2-{2-[4-(4-Hydroxy-piperidin-1-ylmethyl)-2-methyl-phenyl]-2-oxo-ethyl}-5-(5-methoxy-pyridin-2-ylmethoxy)-2H-pyridazin-3-one |
| 9.3 | 5-(5-Methoxy-pyridin-2-ylmethoxy)-2-[2-(2-methyl-4-pyrrolidin-1-ylmethyl-phenyl)-2-oxo-ethyl]-2H-pyridazin-3-one |
| 9.4 | 5-(5-Methoxy-pyridin-2-ylmethoxy)-2-[2-(2-methyl-4-methylaminomethyl-phenyl)-2-oxo-ethyl]-2H-pyridazin-3-one |
| 9.5 | 2-[2-(4-Ethylaminomethyl-2-methyl-phenyl)-2-oxo-ethyl]-5-(5-methoxy-pyridin-2-ylmethoxy)-2H-pyridazin-3-one |
| 10.1 | 2-{2-[4-(1-Dimethylamino-ethyl)-2-methyl-phenyl]-2-oxo-ethyl}-5-(5-methoxy-pyridin-2-ylmethoxy)-2H-pyridazin-3-one |
| 10.2 | 5-(5-Methoxy-pyridin-2-ylmethoxy)-2-{2-[2-methyl-4-(1-methylamino-ethyl)-phenyl]-2-oxo-ethyl}-2H-pyridazin-3-one | including any tautomers and stereoisomers thereof, or a salt thereof or a solvate or hydrate thereof.

The compounds according to the invention and their intermediates may be obtained using methods of synthesis which are known to the one skilled in the art and described in the literature of organic synthesis. Preferably the compounds are obtained analogously to the methods of preparation explained To obtain a compound of general formula (1-3) according to scheme 1, a compound of general formula (1-1) is reacted with a compound of general formula (1-2) in the presence of a base. Suitable bases are particularly inorganic bases such as carbonates, especially cesium carbonate and potassium carbonate. Suitable leaving groups (LG) are preferably selected from bromide, chloride, iodide, trifluoroacetate, trifluoromethanesulfonate, methanesulfonate and toluenesulfonate and the like. The reaction is preferably carried out in an inert organic solvent such as DMF, N,N-dimethylacetamide, DMSO, acetonitrile, THF, methylene chloride or a mixture of solvents. The reaction usually takes place within 2 to 48 hours. Preferred reaction temperatures are between 0° C. and 150° C. Ortho-methyl acetophenone precursors for the synthesis of a compounds of general formula (1-1) can be prepared from the corresponding ortho-methyl aryl iodides or bromides via Heck reaction with alkyl vinyl ethers followed by hydrolysis of the vinyl ether, for instance as described in J. Org. Chem. 2001, 66, 4340-4343.

To obtain a compound of general formula (1-4) according to scheme 1, the alcohol function in compounds of the general formula (1-3) is transferred into a leaving group. Suitable leaving groups (LG) are preferably selected from bromide, chloride, iodide, trifluoroacetate, trifluoromethanesulfonate, methanesulfonate and toluenesulfonate and the like. The methods for preparing the mentioned leaving groups are known to the one skilled in the art and are described in the literature of organic synthesis.

To obtain a compound of general formula (1-5) according to scheme 1, a compound of general formula (1-4) is reacted with an amine $HNR^1R^2$. The amine $HNR^1R^2$ is used in excess (about 2 to 4 mol equivalents based on the compound 1-4). In case of valuable amines $HNR^1R^2$ or amines $HNR^1R^2$ being present as salts, for instance as the hydrochloride salts, a non nucleophilic organic base, preferably triethylamine, diisopropyl-ethylamine, potassium carbonate or cesium carbonate, can be added, so that only 1.0 equivalent of $HNR^1R^2$ has to be used. The reactions are preferably carried out in an inert organic solvent like DMF, N,N-dimethylacetamide, methylene chloride, acetonitrile or THF, or mixtures thereof. DMF and N,N-dimethylacetamide are preferred solvents. The reaction usually takes place within 2 to 48 hours. A preferred temperature range for this reaction is 20° C. to 150° C., preferably 20° C. to 80° C.

known to the one skilled in the art and are described in the literature of organic synthesis.

To obtain a compound of general formula (2-5) according to scheme 2, a compound of general formula (2-4) is reacted with an amine $HNR^1R^2$. The amine $HNR^1R^2$ is used in excess (about 2 to 4 mol equivalents based on the compound 2-4). In case of valuable amines $HNR^1R^2$ or amines $HNR^1R^2$ being present as salts, for instance the hydrochloride salts, a non nucleophilic organic base, preferably triethylamine, diisopropyl-ethylamine, potassium carbonate or cesium carbonate, can be added, so that only 1.0 equivalent of $HNR^1R^2$ has to be used. The reactions are preferably carried out in an inert organic solvent like DMF, N,N-dimethylacetamide, methylene chloride, acetonitrile or THF, or mixtures thereof. DMF is the preferred solvent. The reaction usually takes place within 2 to 48 hours. A preferred temperature range for this reaction is 0° C. to 150° C., preferably 20° C. to 80° C.

The synthetic routes presented may rely on the use of protecting groups. For example reactive groups present, such Scheme 2:

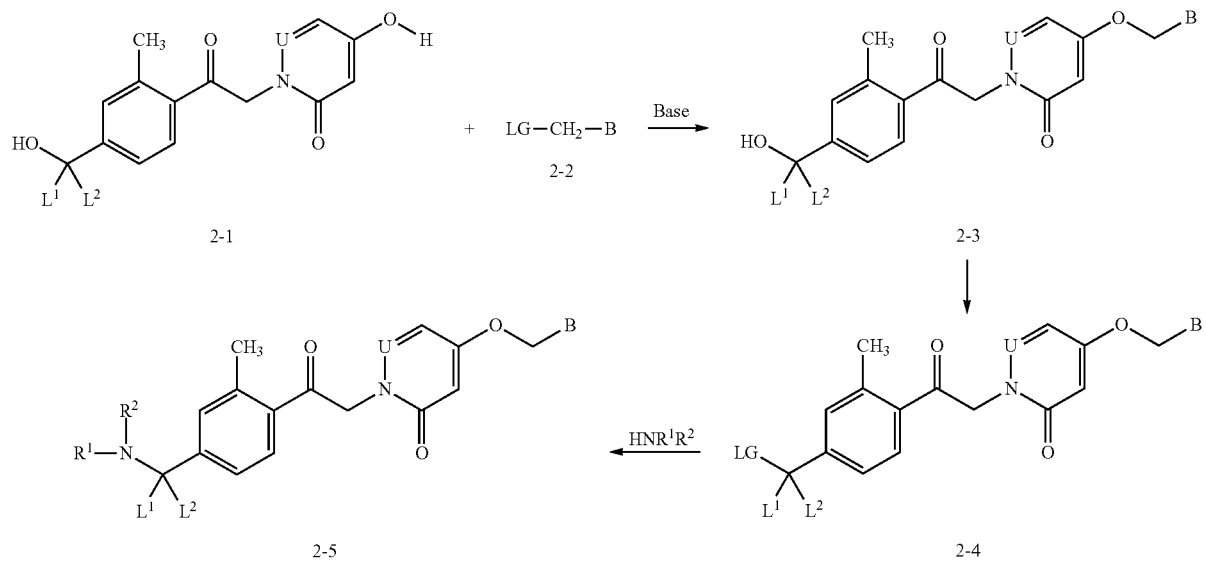

To obtain a compound of general formula (2-3) according to scheme 2, a compound of general formula (2-1) is reacted with a compound of general formula (2-2) in the presence of a base. Suitable bases are particularly inorganic bases such as carbonates, especially potassium carbonate. Suitable leaving groups (LG) are preferably selected from bromide, chloride, iodide, trifluoroacetate, trifluoromethanesulfonate, methanesulfonate and toluenesulfonate and the like. The reaction is preferably carried out in an inert organic solvent such as DMF, acetonitrile, THF, methylene chloride or a mixture of solvents. DMF is the preferred solvent. The reaction usually takes place within 2 to 48 hours. Preferred reaction temperatures are between −20° C. and 120° C., preferably 0° C. to 60° C.

To obtain a compound of general formula (2-4) according to scheme 2, the alcohol function in compounds of the general formula (2-3) is transferred into a leaving group. Suitable leaving groups (LG) are preferably selected from bromide, chloride, iodide, trifluoroacetate, trifluoromethanesulfonate, methanesulfonate and toluenesulfonate and the like. The methods for preparing the mentioned leaving groups are as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents.

As mentioned above, the compounds of formula I may be converted into salts, particularly for pharmaceutical use into the pharmaceutically acceptable salts, for example into the chlorides. As used herein, "pharmaceutically acceptable salts" refer to derivatives of the disclosed compounds wherein the parent compound is modified by making acid or base salts thereof, for example salts with hydrochloric acid.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula I", "compound(s) of the invention" and the like denote the compounds of the formula I according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the deactivation of the melanin-concentrating hormone (MCH), in particular blockade or antagonism of the MCH receptor 1 with one or more compounds of the present invention.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference 85 cm in men and 90 cm in women (see e.g. investigating committee for the diagnosis of metabolic syndrome in Japan).

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or the group to which the substituent is attached.

For example, the term "3-carboxypropyl-group" represents the following substituent:

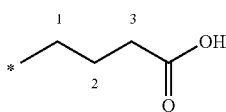

wherein the carboxy group is attached to the third carbon atom of the propyl group. The terms "1-methylpropyl-", "2,2-dimethylpropyl-" or "cyclopropylmethyl-" group represent the following groups:

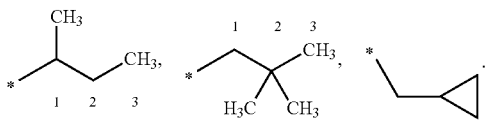

The asterisk may be used in sub-formulas to indicate the bond which is connected to the core molecule as defined.

In a definition of a group the term "wherein each X, Y and Z group is optionally substituted with" or interchangeably "wherein each X, Y and Z group may be substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$" or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. A preferred example are chlorides of the compound according to the invention.

Salts of acids which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example, the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example, the term $C_{1-4}$-alkylene includes —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbornyl, norcaryl, adamantyl, etc.

Many of the terms given above may be used repeatedly in the definition of a formula or group and in each case have one of the meanings given above, independently of one another.

Pharmacological Activity

The compounds according to the present invention, including the physiologically acceptable salts, are effective as antagonists of the MCH receptor, particularly the MCH-1 receptor, and exhibit good affinity in MCH receptor binding studies. Furthermore the compounds according to the invention have an improved metabolic stability. An improved metabolic stability in an in vitro test system, for example incubation with human hepatocytes, typically results in a reduced total body clearance (CL). To achieve a given systemic exposure (area under the curve, AUC) the drug can typically be dosed in a lower amount. The pharmacokinetic relationship describing this relationship is CL/F=Dose/AUC (F corresponds to oral bioavailability). Lower dosages have the advantages of lower drug load of parent drug and metabolites for the patient and lower production costs for the drug product. Pharmacological test systems for MCH-antagonistic properties as well as for metabolic stability are described in the following experimental section.

As antagonists of the MCH receptor the compounds according to the invention are advantageously suitable as pharmaceutical active substances for the treatment of conditions and/or diseases caused by MCH or causally connected with MCH in some other way. Generally the compounds according to the invention have low toxicity, they are well absorbed by oral route and have good intracerebral transitivity, particularly brain accessibility.

Therefore, MCH antagonists which contain at least one compound according to the invention are particularly suitable in mammals, in particular humans, for the treatment of conditions or diseases which are caused by MCH or are otherwise causally connected with MCH, in particular conditions or diseases which are mediated by blocking the MCH receptor, in particular MCH-1R.

Diseases or conditions caused by MCH or otherwise causally connected with MCH, in particular diseases or conditions mediated by blocking the MCH receptor are particularly metabolic disorders, such as for example overweight, obesity, and eating disorders, such as for example bulimia, including bulimia nervosa. The indication obesity includes in particular class I obesity, class II obesity, class III obesity, visceral obesity, abdominal obesity, exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity. This range of indications also includes cachexia, anorexia and hyperphagia.

Compounds according to the invention may be particularly suitable for reducing hunger, curbing appetite, controlling eating behaviour and/or inducing a feeling of satiation.

In particular compounds according to the invention may be suitable to reduce food consumption in overweight or obese patients.

In addition, the diseases caused by MCH or otherwise causally connected with MCH also include hyperlipidaemia, cellulitis, fatty accumulation, malignant mastocytosis, systemic mastocytosis, emotional disorders, affectivity disorders, depression, anxiety states, reproductive disorders, sexual disorders, memory disorders, epilepsy, forms of dementia and hormonal disorders.

Compounds according to the invention are also suitable as active substances for the treatment of other illnesses and/or disorders, particularly those which accompany obesity, such as for example diabetes, diabetes mellitus, particularly type II diabetes mellitus, hyperglycaemia, particularly chronic hyperglycaemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis and gonitis.

MCH antagonists and formulations according to the invention may advantageously be used in combination with a dietary therapy, such as for example a dietary diabetes treatment, and exercise.

Furthermore compounds according to the invention may be suitable in the treatment of obesity in conjunction with a calorie-reduced diet.

Furthermore compounds according to the invention may be suitable for inducing weight loss and/or maintaining of weight loss in in conjunction with a calorie-reduced diet, in particular in obese or overweight patients.

Furthermore compounds according to the invention may be suitable for reducing body weight in overweight or obese patients, in particular in conjunction with a calorie-reduced diet.

The treatment with one or more compounds according to the invention is preferred in obese patients with an initial body mass index (BMI) greater or equal 30 kg/m², or in overweight patients with an initial BMI greater or equal 27 kg/m², in particular in obese or overweight patients in the presence of weight-related comorbidities.

Another range of indications for which the compounds according to the invention are advantageously suitable is the treatment of micturition disorders, such as for example urinary incontinence, hyperactive bladder, urgency, nycturia, enuresis, while the hyperactive bladder and urgency may or may not be connected with benign prostatic hyperplasia.

Generally speaking, the compounds according to the invention are potentially suitable for treating dependencies, such as for example alcohol and/or nicotine dependency, and/or withdrawal symptoms, such as for example weight gain in smokers coming off nicotine. By "dependency" is generally meant here an irresistible urge to take an addictive substance and/or to perform certain actions, particularly in order to either achieve a feeling of wellbeing or to eliminate negative emotions. In particular, the term "dependency" is used here to denote a dependency on an addictive substance. By "withdrawal symptoms" are meant here, in general, symptoms which occur or may occur when addictive substances are withdrawn from patients dependent on one or more such substances. The compounds according to the invention are potentially suitable particularly as active substances for reducing or ending tobacco consumption, for the treatment of a nicotine dependency and/or for the treatment or prevention of nicotine withdrawal symptoms, for reducing the craving for tobacco and/or nicotine and generally as an anti-smoking agent. The compounds according to the invention may also be useful for preventing or at least reducing the weight gain typically seen when smokers are coming off nicotine. The substances may also be suitable as active substances which prevent or at least reduce the craving for and/or relapse into a dependency on addictive substances. The term addictive substances refers particularly but not exclusively to substances with a psycho-motor activity, such as narcotics or drugs, particularly alcohol, nicotine, cocaine, amphetamine, opiates, benzodiazepines and barbiturates.

Furthermore compounds according to the invention may be suitable in the treatment of intestinal inflammation such as cause by inflammatory bowel disease, colitis and/or Crohn's disease. The assessment of activity of compounds of formula I may be carried out employing the assays as described in Kokkotou, E. et al., "Melanin-concentrating hormone as a mediator of intestinal inflammation", PNAS, 105 (30); 10613-10618.

The dosage required to achieve such one or more the effect as described hereinbefore is conveniently, by intravenous or subcutaneous route, 0.001 to 30 mg/kg of body weight, preferably 0.01 to 5 mg/kg of body weight, and by oral administration, 0.01 to 50 mg/kg of body weight, preferably 0.05 to 10 mg/kg of body weight, in each case 1 to 3× daily. A preferred embodiment is an oral administration once or twice daily. A single dose for a human patient is for example in the range from 1 to 200 mg once or twice daily.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

Pharmaceutical Compositions

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, for example carriers and/or diluents.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

Other features and advantages of the present invention will become apparent from the following more detailed Examples which illustrate, by way of example, the principles of the invention.

EXAMPLES

Preliminary Remarks:

As a rule, $^1$H-NMR and/or mass spectra have been obtained for the examples of the invention. The $R_f$ values are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation.

The HPLC data given are measured under the following conditions:

| method A: | analytical column: |
|---|---|
| | Waters, Xbridge C18, 3.0 × 30 mm, 2.5 μm |
| | column temperature: room temperature |
| | Solvent A: 0.1% NH$_3$ in water |
| | Solvent B: 0.1% NH$_3$ in acetonitrile |

| time in min | % A | % B | flow rate in ml/min |
|---|---|---|---|
| 0.00 | 95.0 | 5.0 | 1.40 |
| 1.80 | 10.0 | 90.0 | 1.40 |
| 2.00 | 10.0 | 90.0 | 1.40 |
| 2.20 | 95.0 | 5.0 | 1.40 |

| method B: | analytical column: |
|---|---|
| | Waters, Xbridge C18, 3.0 × 30 mm, 2.5 μm |
| | column temperature: room temperature |
| | Solvent A: 0.1% HCOOH in water |
| | Solvent B: 0.1% HCOOH in acetonitrile |

| time in min | % A | % B | flow rate in ml/min |
|---|---|---|---|
| 0.00 | 95.0 | 5.0 | 1.60 |
| 0.10 | 95.0 | 5.0 | 1.60 |
| 1.75 | 5.0 | 95.0 | 1.60 |
| 1.90 | 5.0 | 95.0 | 1.60 |
| 1.95 | 95.0 | 5.0 | 1.60 |
| 2.00 | 95.0 | 5.0 | 1.60 |

| method C: | analytical column: |
|---|---|
| | Waters, Xbridge C18, 4.6 × 30 mm, 3.5 μm |
| | column temperature: 60° C. |
| | Solvent A: 0.1% NH$_3$ in water |
| | Solvent B: methanol |

| time in min | % A | % B | flow rate in ml/min |
|---|---|---|---|
| 0.00 | 95.0 | 5.0 | 4.0 |
| 0.15 | 95.0 | 5.0 | 4.0 |
| 1.70 | 0.0 | 100.0 | 4.0 |
| 2.10 | 0.0 | 100.0 | 4.0 |

| method D: | analytical column: |
|---|---|
| | Waters, Sunfire C18, 3.0 × 30 mm, 2.5 μm |
| | column temperature: 60° C. |
| | Solvent A: 0.1% TFA in water |
| | Solvent B: methanol |

| time in min | % A | % B | flow rate in ml/min |
|---|---|---|---|
| 0.00 | 95.0 | 5.0 | 2.2 |
| 0.05 | 95.0 | 5.0 | 2.2 |
| 1.40 | 0.0 | 100.0 | 2.2 |
| 1.80 | 0.0 | 100.0 | 2.2 |

| method E: | analytical column: |
|---|---|
| | Waters, Xbridge C18, 3.0 × 30 mm, 2.5 μm |
| | column temperature: 60° C. |
| | Solvent A: 0.1% NH$_3$ in water |
| | Solvent B: methanol |

| time in min | % A | % B | flow rate in ml/min |
|---|---|---|---|
| 0.00 | 95.0 | 5.0 | 2.2 |
| 0.05 | 95.0 | 5.0 | 2.2 |
| 1.40 | 0.0 | 100.0 | 2.2 |
| 1.80 | 0.0 | 100.0 | 2.2 |

| method F: | analytical column: |
|---|---|
| | Waters, StableBond C18, 3.0 × 30 mm, 1.8 μm |
| | column temperature: 60° C. |
| | Solvent A: 0.1% TFA in water |
| | Solvent B: methanol |

| time in min | % A | % B | flow rate in ml/min |
|---|---|---|---|
| 0.00 | 95.0 | 5.0 | 2.2 |
| 0.05 | 95.0 | 5.0 | 2.2 |
| 1.40 | 0.0 | 100.0 | 2.2 |
| 1.80 | 0.0 | 100.0 | 2.2 |

| method G: | analytical column: |
|---|---|
| | Zorbax, StableBond C18, 3.0 × 30 mm, 1.8 μm |
| | column temperature: room temperature |
| | Solvent A: 0.1% HCOOH in water |
| | Solvent B: 0.1% HCOOH in acetonitrile |

| time in min | % A | % B | flow rate in ml/min |
|---|---|---|---|
| 0.00 | 95.0 | 5.0 | 1.4 |
| 0.10 | 95.0 | 5.0 | 1.4 |
| 1.75 | 5.0 | 95.0 | 1.4 |
| 1.90 | 5.0 | 95.0 | 1.4 |

The melting points of crystalline compounds of the invention or salts thereof are determined by Differential Scanning calorimetry (DSC) and evaluated by the onset temperature. The heating rate of the experiments are 10° C./min. The values are determined using a DSC instrument from the O-series™ of TA Instruments.

The following abbreviations are used above and hereinafter:

BOC tert-Butylcarbonate
cal. Calculated
CDI 1,1'-Carbonyl-di-imidazole
CO Carbon monoxide
DCM Dichloromethane
DMAP Dimethyl-pyridin-4-yl-amine
DMF N,N-Dimethylformamide
DMSO Dimethylsulfoxide
EII Electron impact ionisation
ESI Electron spray ionisation
EtOAc Ethyl acetate
h Hour
HCl Hydrochloric acid
Hg Mercury
hPa hecto Pascale
HPLC High pressure liquid chromatography
K$_2$CO$_3$ Potassium crabonate
KHSO$_4$ Potassium hydrogen sulfate
MeOH Methanol
MgSO$_4$ Magnesium sulfate
min Minutes
Na$_2$CO$_3$ Sodium carbonate
NaHCO$_3$ Sodiumhydrogencarbonate
NH$_3$ Ammonia
NH$_4$OH Ammoniumhydroxide OMe Methoxy
Pd/C Palladium on charcoal
PE Petrolether
RT Ambient temperature or room temperature (approx. 20° C.)
TFA Trifluoro acidic acid
THF Tetrahydrofuran Preparation of Starting Materials Preparation 1

4-Benzyloxy-1-[2-(4-bromomethyl-2-methyl-phenyl)-2-oxo-ethyl]-1H-pyridin-2-one

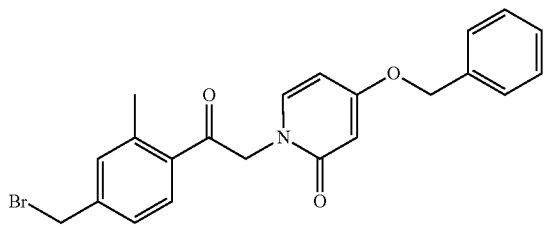 [SMILES: Cc1cc(CBr)ccc1C(=O)Cn1ccc(OCc2ccccc2)cc1=O]

1a 1-(4-Hydroxymethyl-2-methyl-phenyl)-ethanone

To a solution of (4-iodo-3-methylphenyl)methanol (9.70 g, 39.1 mol) in a mixture of water (25 mL) and DMF (100 mL) is added under argon $K_2CO_3$ (6.49 g, 46.9 mmol), palladium (II) acetate (263 mg, 1.17 mmol), 1,3-bis(diphenylphosphino)-propane (1064 mg, 2.58 mmol), LiCl (4.14 g, 97.7 mmol) and butyl vinyl ether (12.7 mL, 97.7 mmol). The mixture is heated at 90° C. for 7 h. After cooling to room temperature, 1 N aqueous HCl (50 mL) is added and the mixture is stirred for 30 min. The mixture is diluted with EtOAc and washed with aqueous $K_2CO_3$ solution. The organic layer is dried over $MgSO_4$, concentrated under reduced pressure and purified chromatographically (silica gel, cyclohexane/EtOAc 7:3).
Yield: 3.60 g (56% of theory)
ESI mass spectrum: $[M+H]^+=165$
$R_f$-value: 0.14 (silica gel, cyclohexane/EtOAc 7:3)

1b 2-Bromo-1-(4-hydroxymethyl-2-methyl-phenyl)-ethanone

To a solution of 1-(4-hydroxymethyl-2-methyl-phenyl)-ethanone (preparation 1a, 600 mg, 3.65 mmol) in $CH_2Cl_2$ (25 mL) is added tetrabutylammonium tribromide in several portions (1.76 g, 3.65 mmol). The reaction mixture is stirred for 30 min at room temperature. After washing with water, the organic layer is dried over $MgSO_4$ and concentrated under reduced pressure. The remaining residue is dissolved in hexanes/EtOAc 3:7 and filtered over silica gel.
Yield: 890 mg (quantitative)
ESI mass spectrum: $[M+H]^+=243$ 1c 4-Benzyloxy-1-[2-(4-hydroxymethyl-2-methyl-phenyl)-2-oxo-ethyl]-1H-pyridin-2-one To a solution of 4-benzyloxy-1H-pyridin-2-one (728 mg, 3.62 mmol) in DMSO (4.00 mL) is added cesium carbonate (2.95 g, 9.05 mmol) and the mixture is stirred 15 min at room temperature. 2-Bromo-1-(4-hydroxymethyl-2-methyl-phenyl)-ethanone (preparation 1b, 880 mg, 3.62 mmol) is added in portions and the mixture and is stirred 2 h at room temperature. After addition of water, the precipitate is collected, washed with water and dried.
Yield: 1.10 g (84% of theory)
ESI mass spectrum: $[M+H]^+=364$
Retention time HPLC: 1.57 min (METHOD A).

1d 4-Benzyloxy-1-[2-(4-bromomethyl-2-methyl-phenyl)-2-oxo-ethyl]-1H-pyridin-2-one To a solution of 4-benzyloxy-1-[2-(4-hydroxymethyl-2-methyl-phenyl)-2-oxo-ethyl]-1H-pyridin-2-one (preparation 1c, 1.10 g, 3.03 mmol) in $CH_2Cl_2$ (20 mL) is added slowly phosphorus tribromide (199 µL, 2.12 mmol) at 0° C. The cooling bath is removed and the mixture is stirred for 1 h at room temperature. After cooling, the reaction mixture is quenched with aqueous $NaHCO_3$ solution and extracted with $CH_2Cl_2$. The organic layer is washed with water, dried over $MgSO_4$, and concentrated under reduced pressure.
Yield: 650 mg (50% of theory)
ESI mass spectrum: $[M+H]^+=426$
Retention time HPLC: 1.84 min (METHOD A).

Preparation 2

1-[2-(4-Bromomethyl-2-methyl-phenyl)-2-oxo-ethyl]-4-(5-fluoro-pyridin-2-ylmethoxy)-1H-pyridin-2-one

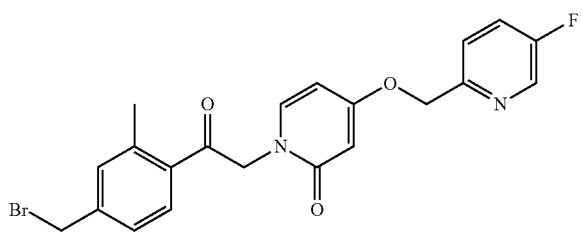

2a 4-(5-Fluoro-pyridin-2-ylmethoxy)-1-[2-(4-hydroxymethyl-2-methyl-phenyl)-2-oxo-ethyl]-1H-pyridin-2-one 4-(5-Fluoro-pyridin-2-ylmethoxy)-1-[2-(4-hydroxymethyl-2-methyl-phenyl)-2-oxo-ethyl]-1H-pyridin-2-one is prepared following preparation 1c employing 4-(5-fluoro-pyridin-2-ylmethoxy)-1H-pyridin-2-one (described in WO 09/103,478) instead of 4-benzyloxy-1H-pyridin-2-one.
Yield: 90% of theory
ESI mass spectrum: $[M+H]^+=383$
Retention time HPLC: 1.42 min (METHOD A).

2b 1-[2-(4-Bromomethyl-2-methyl-phenyl)-2-oxo-ethyl]-4-(5-fluoro-pyridin-2-ylmethoxy)-1H-pyridin-2-one 1-[2-(4-Bromomethyl-2-methyl-phenyl)-2-oxo-ethyl]-4-(5-fluoro-pyridin-2-ylmethoxy)-1H-pyridin-2-one is prepared following preparation 1d employing 4-(5-fluoro-pyridin-2-ylmethoxy)-1-[2-(4-hydroxymethyl-2-methyl-phenyl)-2-oxo-ethyl]-1H-pyridin-2-one (preparation 2a) instead of preparation 1c.

Yield: 93% of theory
ESI mass spectrum: [M+H]$^+$=445
Retention time HPLC: 1.72 min (METHOD A).

Preparation 3

1-[2-(4-Bromomethyl-2-methyl-phenyl)-2-oxo-ethyl]-4-(5-chloro-pyridin-2-ylmethoxy)-1H-pyridin-2-one

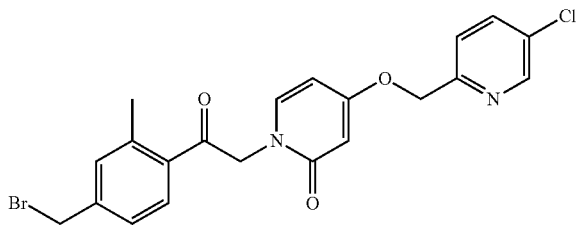 [SMILES: Cc1cc(CBr)ccc1C(=O)Cn1ccc(OCc2ccc(Cl)cn2)cc1=O]

3a 4-(5-Chloro-pyridin-2-ylmethoxy)-1-[2-(4-hydroxymethyl-2-methyl-phenyl)-2-oxo-ethyl]-1H-pyridin-2-one 4-(5-Chloro-pyridin-2-ylmethoxy)-1-[2-(4-hydroxymethyl-2-methyl-phenyl)-2-oxo-ethyl]-1H-pyridin-2-one is prepared following preparation 1c employing 4-(5-chloro-pyridin-2-ylmethoxy)-1H-pyridin-2-one (described in WO 09/103,478) instead of 4-benzyloxy-1H-pyridin-2-one.
Yield: 99% of theory
ESI mass spectrum: [M+H]$^+$=399
Retention time HPLC: 1.50 min (METHOD A).

3b 1-[2-(4-Bromomethyl-2-methyl-phenyl)-2-oxo-ethyl]-4-(5-chloro-pyridin-2-ylmethoxy)-1H-pyridin-2-one 1-[2-(4-Bromomethyl-2-methyl-phenyl)-2-oxo-ethyl]-4-(5-chloro-pyridin-2-ylmethoxy)-1H-pyridin-2-one is prepared following preparation 1d employing 4-(5-chloro-pyridin-2-ylmethoxy)-1-[2-(4-hydroxymethyl-2-methyl-phenyl)-2-oxo-ethyl]-1H-pyridin-2-one (preparation 3a) instead of preparation 1c.
Yield: 90% of theory
ESI mass spectrum: [M+H]$^+$=461
Retention time HPLC: 1.80 min (METHOD A).

Preparation 4

1-[2-(4-Bromomethyl-2-methyl-phenyl)-2-oxo-ethyl]-4-(5-bromo-pyridin-2-ylmethoxy)-1H-pyridin-2-one

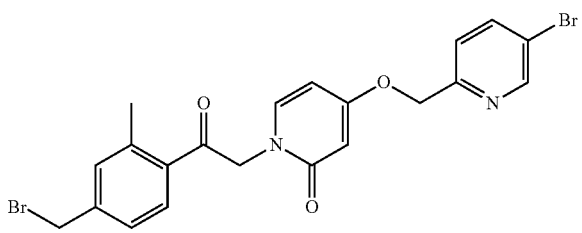 [SMILES: Cc1cc(CBr)ccc1C(=O)Cn1ccc(OCc2ccc(Br)cn2)cc1=O]

4a 4-(5-Bromo-pyridin-2-ylmethoxy)-1-[2-(4-hydroxymethyl-2-methyl-phenyl)-2-oxo-ethyl]-1H-pyridin-2-one 4-(5-Bromo-pyridin-2-ylmethoxy)-1-[2-(4-hydroxymethyl-2-methyl-phenyl)-2-oxo-ethyl]-1H-pyridin-2-one is prepared following preparation 1c employing 4-(5-bromo-pyridin-2-ylmethoxy)-1H-pyridin-2-one (described in WO 09/103,478) instead of 4-benzyloxy-1H-pyridin-2-one.
Yield: 98% of theory
ESI mass spectrum: [M+H]$^+$=443
Retention time HPLC: 1.54 min (METHOD A).

4b 1-[2-(4-Bromomethyl-2-methyl-phenyl)-2-oxo-ethyl]-4-(5-bromo-pyridin-2-ylmethoxy)-1H-pyridin-2-one 1-[2-(4-Bromomethyl-2-methyl-phenyl)-2-oxo-ethyl]-4-(5-bromo-pyridin-2-ylmethoxy)-1H-pyridin-2-one is prepared following preparation 1d employing 4-(5-bromo-pyridin-2-ylmethoxy)-1-[2-(4-hydroxymethyl-2-methyl-phenyl)-2-oxo-ethyl]-1H-pyridin-2-one (preparation 4a) instead of preparation 1c.
Yield: 88% of theory
ESI mass spectrum: [M+H]$^+$=505
Retention time HPLC: 1.81 min (METHOD A).

Preparation 5

5-Benzyloxy-2-[2-(4-bromomethyl-2-methyl-phenyl)-2-oxo-ethyl]-2H-pyridazin-3-one

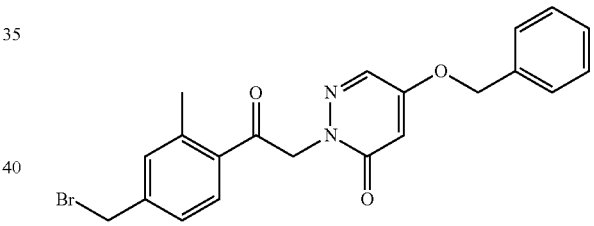

5a 5-Benzyloxy-2-[2-(4-hydroxymethyl-2-methyl-phenyl)-2-oxo-ethyl]-2H-pyridazin-3-one 5-Benzyloxy-2-[2-(4-hydroxymethyl-2-methyl-phenyl)-2-oxo-ethyl]-2H-pyridazin-3-one is prepared following preparation 1c employing 5-benzyloxy-2H-pyridazin-3-one (described in WO 09/103,478) instead of 4-benzyloxy-1H-pyridin-2-one.
Yield: 81% of theory
ESI mass spectrum: [M+H]$^+$=365
Retention time HPLC: 1.63 min (METHOD A).

5b 5-Benzyloxy-2-[2-(4-bromomethyl-2-methyl-phenyl)-2-oxo-ethyl]-2H-pyridazin-3-one 5-Benzyloxy-2-[2-(4-bromomethyl-2-methyl-phenyl)-2-oxo-ethyl]-2H-pyridazin-3-one is prepared following preparation 1d employing 5-benzyloxy-2-[2-(4-hydroxymethyl-2-methyl-phenyl)-2-oxo-ethyl]-2H-pyridazin-3-one (preparation 5a) instead of preparation 1c.
Yield: 93% of theory
ESI mass spectrum: [M+H]$^+$=427
Retention time HPLC: 1.93 min (METHOD A).

Preparation 6

2-[2-(4-Bromomethyl-2-methyl-phenyl)-2-oxo-ethyl]-5-(5-fluoro-pyridin-2-ylmethoxy)-2H-pyridazin-3-one

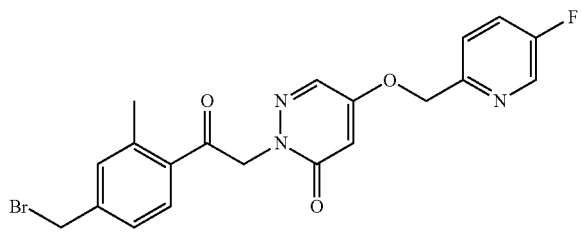 [SMILES: Cc1cc(CBr)ccc1C(=O)Cn1ncc(OCc2ccc(F)cn2)cc1=O]

6a 5-(5-Fluoro-pyridin-2-ylmethoxy)-2-[2-(4-hydroxymethyl-2-methyl-phenyl)-2-oxo-ethyl]-2H-pyridazin-3-one 5-(5-Fluoro-pyridin-2-ylmethoxy)-2-[2-(4-hydroxymethyl-2-methyl-phenyl)-2-oxo-ethyl]-2H-pyridazin-3-one is prepared following preparation 1c employing 5-(5-fluoro-pyridin-2-ylmethoxy)-2H-pyridazin-3-one (described in WO 09/103,478) instead of 4-benzyloxy-1H-pyridin-2-one.
Yield: 91% of theory
ESI mass spectrum: $[M+H]^+=384$
Retention time HPLC: 1.46 min (METHOD A).

6b 2-[2-(4-Bromomethyl-2-methyl-phenyl)-2-oxo-ethyl]-5-(5-fluoro-pyridin-2-ylmethoxy)-2H-pyridazin-3-one 2-[2-(4-Bromomethyl-2-methyl-phenyl)-2-oxo-ethyl]-5-(5-fluoro-pyridin-2-ylmethoxy)-2H-pyridazin-3-one is prepared following preparation 1d employing 5-(5-fluoro-pyridin-2-ylmethoxy)-2-[2-(4-hydroxymethyl-2-methyl-phenyl)-2-oxo-ethyl]-2H-pyridazin-3-one (preparation 6a) instead of preparation 1c.
Yield: 92% of theory
ESI mass spectrum: $[M+H]^+=446$
Retention time HPLC: 1.78 min (METHOD A).

Preparation 7

2-[2-(4-Bromomethyl-2-methyl-phenyl)-2-oxo-ethyl]-5-(5-chloro-pyridin-2-ylmethoxy)-2H-pyridazin-3-one

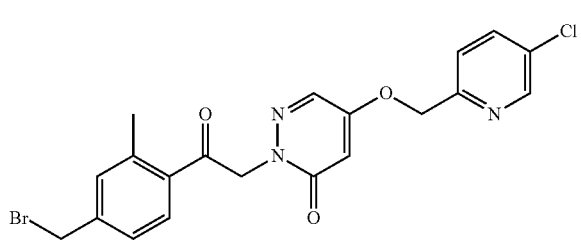 [SMILES: Cc1cc(CBr)ccc1C(=O)Cn1ncc(OCc2ccc(Cl)cn2)cc1=O]

7a 5-(5-Chloro-pyridin-2-ylmethoxy)-2-[2-(4-hydroxymethyl-2-methyl-phenyl)-2-oxo-ethyl]-2H-pyridazin-3-one 5-(5-Chloro-pyridin-2-ylmethoxy)-2-[2-(4-hydroxymethyl-2-methyl-phenyl)-2-oxo-ethyl]-2H-pyridazin-3-one is prepared following preparation 1c employing 5-(5-chloro-pyridin-2-ylmethoxy)-2H-pyridazin-3-one (described in WO 09/103,478) instead of 4-benzyloxy-1H-pyridin-2-one.
Yield: 91% of theory
ESI mass spectrum: $[M+H]^+=400$
Retention time HPLC: 1.54 min (METHOD A).

7b 2-[2-(4-Bromomethyl-2-methyl-phenyl)-2-oxo-ethyl]-5-(5-chloro-pyridin-2-ylmethoxy)-2H-pyridazin-3-one 2-[2-(4-Bromomethyl-2-methyl-phenyl)-2-oxo-ethyl]-5-(5-chloro-pyridin-2-ylmethoxy)-2H-pyridazin-3-one is prepared following preparation 1d employing 5-(5-chloro-pyridin-2-ylmethoxy)-2-[2-(4-hydroxymethyl-2-methyl-phenyl)-2-oxo-ethyl]-2H-pyridazin-3-one (preparation 7a) instead of preparation 1c.
Yield: 83% of theory
ESI mass spectrum: $[M+H]^+=462$
Retention time HPLC: 1.85 min (METHOD A).

Preparation 8

2-[2-(4-Bromomethyl-2-methyl-phenyl)-2-oxo-ethyl]-5-(5-bromo-pyridin-2-ylmethoxy)-2H-pyridazin-3-one

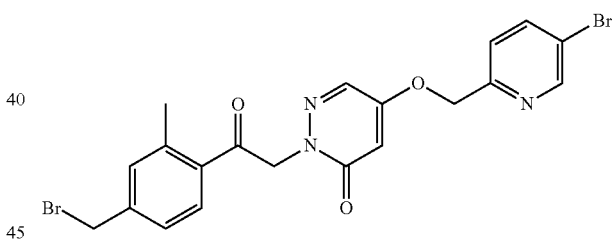

8a 5-(5-Bromo-pyridin-2-ylmethoxy)-2-[2-(4-hydroxymethyl-2-methyl-phenyl)-2-oxo-ethyl]-2H-pyridazin-3-one 5-(5-Bromo-pyridin-2-ylmethoxy)-2-[2-(4-hydroxymethyl-2-methyl-phenyl)-2-oxo-ethyl]-2H-pyridazin-3-one is prepared following preparation 1c employing 5-(5-bromo-pyridin-2-ylmethoxy)-2H-pyridazin-3-one (described in WO 09/103,478) instead of 4-benzyloxy-1H-pyridin-2-one.
Yield: 90% of theory
ESI mass spectrum: $[M+H]^+=444$
Retention time HPLC: 1.58 min (METHOD A).

8b 2-[2-(4-Bromomethyl-2-methyl-phenyl)-2-oxo-ethyl]-5-(5-bromo-pyridin-2-ylmethoxy)-2H-pyridazin-3-one 2-[2-(4-Bromomethyl-2-methyl-phenyl)-2-oxo-ethyl]-5-(5-bromo-pyridin-2-ylmethoxy)-2H-pyridazin-3-one is prepared following preparation 1d employing 5-(5-bromo-pyridin-2-ylmethoxy)-2-[2-(4-hydroxymethyl-2-methyl-phenyl)-2-oxo-ethyl]-2H-pyridazin-3-one (preparation 8a) instead of preparation 1c.

Yield: 59% of theory
ESI mass spectrum: [M+H]$^+$=506

Preparation 9

2-[2-(4-Bromomethyl-2-methyl-phenyl)-2-oxo-ethyl]-5-(5-methoxy-pyridin-2-ylmethoxy)-2H-pyridazin-3-one

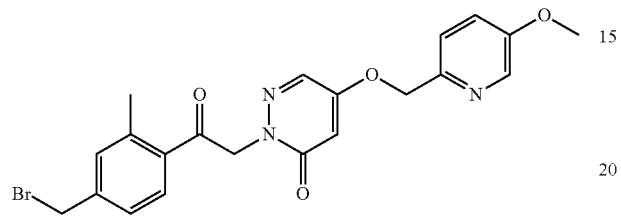

9a 5-(5-Methoxy-pyridin-2-ylmethoxy)-2-(tetrahydro-pyran-2-yl)-2H-pyridazin-3-one To a solution of 5-hydroxy-2-(tetrahydro-pyran-2-yl)-2H-pyridazin-3-one (described in preparation 5a of WO 08/022,979, 705 mg, 3.59 mmol) and (5-methoxy-pyridin-2-yl)-methanol (Milestone Pharmtech, 500 mg, 3.59 mmol) in THF (10 mL) is added polymer-bound triphenylphosphine (2.40 g, 3 mmol/g, 7.2 mmol). After cooling to 0° C., diisopropyl azodicarboxylate (1.42 mL, 7.2 mmol) is added slowly. Afterwards, the reaction mixture is stirred for 3 h at room temperature. The reaction mixture is filtered and the solvent is evaporated. The residue is purified via reverse phase HPLC chromatography (Waters XBridge 5 µm, gradient 5%→90% acetonitrile in water+0.3% NH$_4$OH).

Yield: 500 mg (44% of theory)
ESI mass spectrum: [M+H]$^+$=318
Retention time HPLC: 1.49 min (METHOD A).

9b 5-(5-Methoxy-pyridin-2-ylmethoxy)-2H-pyridazin-3-one

A solution of 5-(5-methoxy-pyridin-2-ylmethoxy)-2-(tetrahydro-pyran-2-yl)-2H-pyridazin-3-one (500 mg, 1.58 mmol) in a mixture of MeOH (5 mL) and concentrated aqueous HCl (0.65 mL) is heated at reflux for 2 h. Most of the volatiles are removed under reduced pressure and water is added. The formed precipitate is filtered off and dried.

Yield: 400 mg (quantitative)
ESI mass spectrum: [M+H]$^+$=234
Retention time HPLC: 1.12 min (METHOD A).

9c 2-[2-(4-Hydroxymethyl-2-methyl-phenyl)-2-oxo-ethyl]-5-(5-methoxy-pyridin-2-ylmethoxy)-2H-pyridazin-3-one 2-[2-(4-Hydroxymethyl-2-methyl-phenyl)-2-oxo-ethyl]-5-(5-methoxy-pyridin-2-ylmethoxy)-2H-pyridazin-3-one is prepared following preparation 1c employing 5-(5-methoxy-pyridin-2-ylmethoxy)-2H-pyridazin-3-one (preparation 9b) instead of 4-benzyloxy-1H-pyridin-2-one.

Yield: 70% of theory
ESI mass spectrum: [M+H]$^+$=396
Retention time HPLC: 1.60 min (METHOD A).

9d 2-[2-(4-Bromomethyl-2-methyl-phenyl)-2-oxo-ethyl]-5-(5-methoxy-pyridin-2-ylmethoxy)-2H-pyridazin-3-one 2-[2-(4-Bromomethyl-2-methyl-phenyl)-2-oxo-ethyl]-5-(5-methoxy-pyridin-2-ylmethoxy)-2H-pyridazin-3-one is prepared following preparation 1d employing 2-[2-(4-hydroxymethyl-2-methyl-phenyl)-2-oxo-ethyl]-5-(5-methoxy-pyridin-2-ylmethoxy)-2H-pyridazin-3-one (preparation 9c) instead of preparation 1c. The reaction mixture is stirred overnight. Tert-butyl methyl ether is added and the resulting precipitate is filtered off and dried.

Yield: 97% of theory
ESI mass spectrum: [M+H]$^+$=458
Retention time HPLC: 1.91 min (METHOD A).

Preparation 10

2-{2-[4-(1-Bromo-ethyl)-2-methyl-phenyl]-2-oxo-ethyl}-5-(5-methoxy-pyridin-2-ylmethoxy)-2H-pyridazin-3-one

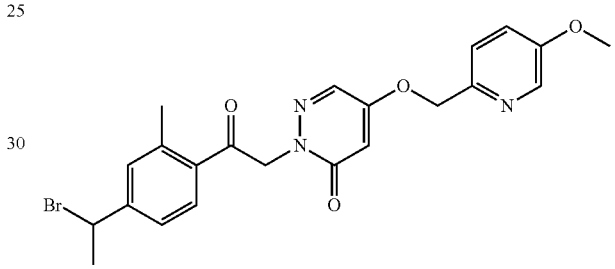

10a 1-[4-(1-Hydroxy-ethyl)-2-methyl-phenyl]ethanone

1-[4-(1-Hydroxy-ethyl)-2-methyl-phenyl]-ethanone is prepared following preparation 1a employing 1-(4-bromo-3-methyl-phenyl)-ethanol instead of (4-iodo-3-methyl-phenyl)methanol.

Yield: 49% of theory 10b 2-Bromo-1-[4-(1-hydroxy-ethyl)-2-methyl-phenyl]ethanone 2-Bromo-1-[4-(1-hydroxy-ethyl)-2-methyl-phenyl]ethanone is prepared following preparation 1b employing 1-[4-(1-hydroxy-ethyl)-2-methyl-phenyl]-ethanone instead of 1-(4-hydroxymethyl-2-methyl-phenyl)-ethanone.

Yield: 82% of theory
ESI mass spectrum: [M+H]$^+$=257

10c 2-{2-[4-(1-Hydroxy-ethyl)-2-methyl-phenyl]-2-oxo-ethyl}-5-(5-methoxy-pyridin-2-ylmethoxy)-2H-pyridazin-3-one To a solution of 5-(5-methoxy-pyridin-2-ylmethoxy)-2H-pyridazin-3-one (preparation 9b, 2.00 g, 8.58 mmol) in DMSO (20 mL) is added cesium carbonate (5.59 g, 17.2 mmol) and the mixture is stirred 10 min at room temperature. Then 2-bromo-1-[4-(1-hydroxy-ethyl)-2-methyl-phenyl]-ethanone (preparation 10b, 2.21 g, 8.58 mmol) is added in portions and the mixture is stirred overnight at room temperature. An additional 0.5 g of the bromoketone is added and the mixture is stirred for 3 h at room temperature. After addition of water, the reaction mixture is extracted with ethyl acetate. The combined organic layer is dried over $MgSO_4$ and evaporated under reduced pressure.

Yield: 2.90 g (74% of theory)
ESI mass spectrum: $[M+H]^+=410$
Retention time HPLC: 0.91 min (METHOD E).

10d 2-{2-[4-(1-Bromo-ethyl)-2-methyl-phenyl]-2-oxo-ethyl}-5-(5-methoxy-pyridin-2-ylmethoxy)-2H-pyridazin-3-one 2-{2-[4-(1-Bromo-ethyl)-2-methyl-phenyl]-2-oxo-ethyl}-5-(5-methoxy-pyridin-2-ylmethoxy)-2H-pyridazin-3-one is prepared following preparation 1d employing 2-{2-[4-(1-Hydroxy-ethyl)-2-methyl-phenyl]-2-oxo-ethyl}-5-(5-methoxy-pyridin-2-ylmethoxy)-2H-pyridazin-3-one instead of preparation 1c.
Yield: 93% of theory
ESI mass spectrum: $[M+H]^+=472$
Retention time HPLC: 1.58 min (METHOD C).

Preparation 11

1-[2-(4-Bromomethyl-2-methyl-phenyl)-2-oxo-ethyl]-4-(5-methoxy-pyridin-2-ylmethoxy)-1H-pyridin-2-one

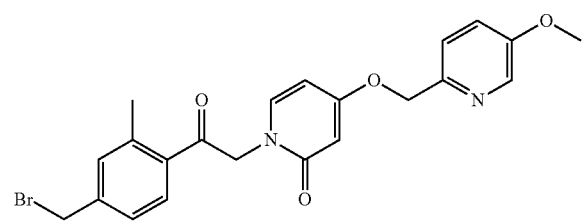 [SMILES: COc1ccc(COc2ccn(CC(=O)c3ccc(CBr)cc3C)c(=O)c2)nc1]

11a 2-Bromomethyl-5-methoxy-pyridine

To a suspension of (5-methoxypyridin-2-yl)-methanol (1.00 g, 7.19 mmol) in $CH_2Cl_2$ (15 mL) is added slowly under cooling phosphorus tribromide (473 µL, 5.03 mmol). The reaction mixture is stirred overnight at room temperature. Tert-Butyl methyl ether (50 mL) is added to the mixture. The formed precipitate is filtered off and dried.
Yield: 2.00 g crude material
ESI mass spectrum: $[M+H]^+=202$
Retention time HPLC: 0.59 (METHOD D).

11b 4-(5-Methoxy-pyridin-2-ylmethoxy)-1H-pyridin-2-one

To a solution of 2-bromomethyl-5-methoxy-pyridine (preparation 11a, 2.00 g crude material), 2,4-dihydroxypyridine (1.06 g, 9.5 mmol) in acetonitrile (20 mL) and DMF (5 mL) is added $K_2CO_3$ and the mixture is stirred for 4 h at 50° C. and overnight at room temperature. The reaction mixture is diluted with water (60 mL) and extracted several times with ethyl acetate. The organic layer is dried over $Na_2SO_4$, concentrated under reduced pressure and purified via reverse phase HPLC chromatography (Waters XBridge 5 µm, gradient 25%→95% methanol in water+0.3% $NH_4OH$).

Yield: 532 mg (29% of theory)
ESI mass spectrum: $[M+H]^+=233$
Retention time HPLC: 0.60 min (METHOD E).

11c 1-[2-(4-Hydroxymethyl-2-methyl-phenyl)-2-oxo-ethyl]-4-(5-methoxy-pyridin-2-ylmethoxy)-1H-pyridin-2-one 1-[2-(4-Hydroxymethyl-2-methyl-phenyl)-2-oxo-ethyl]-4-(5-methoxy-pyridin-2-ylmethoxy)-1H-pyridin-2-one is prepared following preparation 1c employing 4-(5-methoxy-pyridin-2-ylmethoxy)-1H-pyridin-2-one (preparation 11b) instead of 4-benzyloxy-1H-pyridin-2-one.
Yield: 59% of theory
ESI mass spectrum: $[M+H]^+=395$
Retention time HPLC: 0.89 min (METHOD F).

11d 1-[2-(4-Bromomethyl-2-methyl-phenyl)-2-oxo-ethyl]-4-(5-methoxy-pyridin-2-ylmethoxy)-1H-pyridin-2-one 1-[2-(4-Bromomethyl-2-methyl-phenyl)-2-oxo-ethyl]-4-(5-methoxy-pyridin-2-ylmethoxy)-1H-pyridin-2-one is prepared following preparation 1d employing 1-[2-(4-hydroxymethyl-2-methyl-phenyl)-2-oxo-ethyl]-4-(5-methoxy-pyridin-2-ylmethoxy)-1H-pyridin-2-one (preparation 11c) instead of preparation 1c. The reaction mixture is stirred overnight. Tert-butyl methyl ether is added and the resulting precipitate is filtered off and dried.
Yield: 80% of theory
ESI mass spectrum: $[M+H]^+=457$
Retention time HPLC: 1.12 min (METHOD F).

PREPARATION OF EXAMPLE COMPOUNDS

Example 1.1

4-Benzyloxy-1-{2-[4-(3-hydroxy-azetidin-1-ylmethyl)-2-methyl-phenyl]-2-oxo-ethyl}-1H-pyridin-2-one

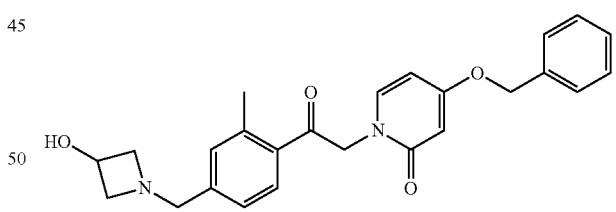

To a solution of 4-benzyloxy-1-[2-(4-bromomethyl-2-methyl-phenyl)-2-oxo-ethyl]-1H-pyridin-2-one (preparation 1d, 72 mg, 0.17 mmol) in DMF (2 mL) is added 3-hydroxyazetidine hydrochloride (56 mg, 0.51 mmol). The reaction mixture is stirred for 30 min at room temperature. The mixture is purified via reverse phase HPLC chromatography (Gilson, Xbridge C18 5 µm, gradient 5%→90% acetonitrile in water+0.3% $NH_4OH$, 120 mL/min).
Yield: 43 mg (61% of theory)
ESI mass spectrum: $[M+H]^+=419$
Retention time HPLC: 1.53 min (METHOD A).

The following examples are prepared as described for Example 1.1, employing the corresponding amines (as free base), respectively.

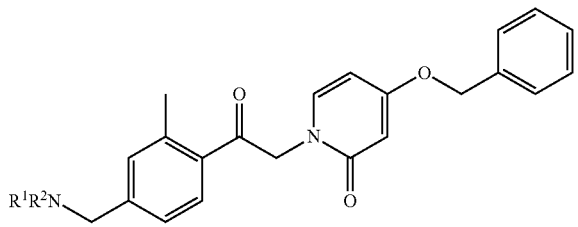
| Example | R¹R²N— | Yield (%) | Formula | MS | Retention time HPLC in min (method) | DSC (melting point) |
|---|---|---|---|---|---|---|
| 1.2 | | 53 | C23H24N2O3 | 377 [M + H]⁺ | 1.62 (A) | |
| 1.3 | | 62 | C27H30N2O4 | 447 [M + H]⁺ | 1.59 (A) | Onset: 156° C. |
| 1.4 | | 64 | C26H28N2O4 | 433 [M + H]⁺ | 1.67 (A) | |
| 1.5 | | 66 | C27H31N3O3 | 446 [M + H]⁺ | 1.60 (A) | |
| 1.6 | | 73 | C28H32N2O4 | 461 [M + H]⁺ | 1.63 (A) | |
| 1.7 | | 60 | C26H28N2O3 | 417 [M + H]⁺ | 1.80 (A) | Onset: 131° C. |
| 1.8 | | 58 | C24H26N2O3 | 391 [M + H]⁺ | 1.70 (A) | Onset: 137° C. |
| 1.9 | | 88 | C27H30N2O3 | 431 [M + H]⁺ | 1.90 (A) | |

4-Benzyloxy-1-{2-[4-(4-hydroxy-piperidin-1-ylmethyl)-2-methyl-phenyl]-2-oxo-ethyl}-1H-pyridin-2-one, monohydrochloride

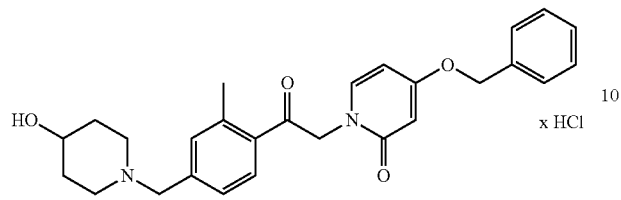

The hydrochloride salt of the compound 1.3 is prepared by adding a 1.1 equivalent of HCl (as 10 M solution of HCl in ethanol) to a concentrated solution of the corresponding free base in refluxing ethanol. The hydrochloride salt, which precipitates upon cooling, is filtered off and dried under reduced pressure. DSC (melting point) of the hydrochloride salt of the compound 1.3: Onset: 217° C.

4-Benzyloxy-1-[2-(2-methyl-4-pyrrolidin-1-ylmethyl-phenyl)-2-oxo-ethyl]-1H-pyridin-2-one, monohydrochloride

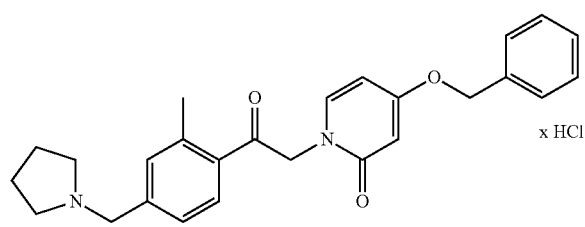 [SMILES: Cc1cc(CN2CCCC2)ccc1C(=O)Cn1ccc(OCc2ccccc2)cc1=O]

The hydrochloride salt of the compound 1.7 is prepared by adding a 1.1 equivalent of HCl (as 10 M solution of HCl in ethanol) to a concentrated solution of the corresponding free base in refluxing ethanol. The hydrochloride salt, which precipitates upon cooling, is filtered off and dried under reduced pressure. DSC (melting point) of the hydrochloride salt of the compound 1.7: Onset: 199° C.

Example 1.10

4-Benzyloxy-1-{2-[4-(3-hydroxy-3-methyl-pyrrolidin-1-ylmethyl)-2-methyl-phenyl]-2-oxo-ethyl}-1H-pyridin-2-one

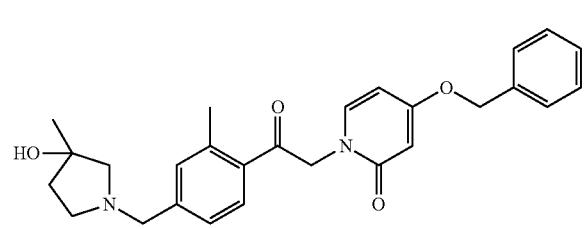 [SMILES: Cc1cc(CN2CCC(C)(O)C2)ccc1C(=O)Cn1ccc(OCc2ccccc2)cc1=O]

To a solution of 4-benzyloxy-1-[2-(4-bromomethyl-2-methyl-phenyl)-2-oxo-ethyl]-1H-pyridin-2-one (preparation 1d, 100 mg, 0.24 mmol) in DMF (2 mL) is added 3-hydroxy-3-methylpyrrolidine (28 mg, 0.28 mmol) and $K_2CO_3$ (65 mg, 0.47 mmol). The reaction mixture is stirred overnight at 50° C. The mixture is purified via reverse phase HPLC chromatography (Phenomenex Gemini-C18 10 μm, gradient 5% 90% acetonitrile in water+0.3% $NH_4OH$, 120 mL/min).

Yield: 75 mg (72% of theory)

ESI mass spectrum: $[M+H]^+=447$

Retention time HPLC: 1.67 min (METHOD A).

The following examples are prepared as described for Example 1.10, employing the corresponding amines, respectively, and N,N-dimethylacetamide (instead of DMF) as solvent.

| Example | $R^1R^2N$— | Yield (%) | Formula | MS | Retention time HPLC in min (method) |
|---|---|---|---|---|---|
| 1.11 | HO-pyrrolidin-3-yl | 59 | C26H28N2O4 | 433 $[M+H]^+$ | 1.61 (A) |
| 1.12 | ethyl(methyl)amino | 78 | C24H26N2O3 | 391 $[M+H]^+$ | 1.74 (A) |
| 1.13 | 3-hydroxypiperidin-1-yl | 86 | C27H30N2O4 | 447 $[M+H]^+$ | 1.66 (A) |
| 1.14 | HO-pyrrolidin-3-yl | 76 | C26H28N2O4 | 433 $[M+H]^+$ | 1.61 (A) |
| 1.15 | 3-hydroxypiperidin-1-yl | 86 | C27H30N2O4 | 447 $[M+H]^+$ | 1.66 (A) |
| 1.16 | 2-(hydroxymethyl)piperidin-1-yl | 59 | C28H32N2O4 | 461 $[M+H]^+$ | 1.77 (A) |

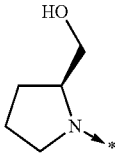

| Example | R¹R²N— | Yield (%) | Formula | MS | Retention time HPLC in min (method) |
|---|---|---|---|---|---|
| 1.17 | 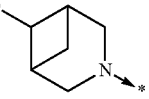 | 75 | C27H30N2O4 | 447 [M+H]⁺ | 1.72 (A) |
| 1.18 | 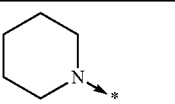 | 37 | C28H30N2O4 | 459 [M+H]⁺ | 1.32 (G) |

Example 2.1

4-(5-Fluoro-pyridin-2-ylmethoxy)-1-[2-(2-methyl-4-pyrrolidin-1-ylmethyl-phenyl)-2-oxo-ethyl]-1H-pyridin-2-one

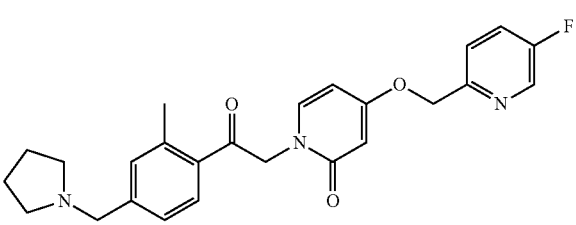 [SMILES: Cc1cc(CN2CCCC2)ccc1C(=O)Cn1ccc(OCc2ccc(F)cn2)cc1=O]

To a solution of 1-[2-(4-bromomethyl-2-methyl-phenyl)-2-oxo-ethyl]-4-(5-fluoro-pyridin-2-ylmethoxy)-1H-pyridin-2-one (preparation 2b, 111 mg, 0.25 mmol) in DMF (2 mL) is added pyrrolidine (63 µL, 0.75 mmol). The reaction mixture is stirred for 60 min at room temperature. The mixture is purified via reverse phase HPLC chromatography (Gilson Xbridge C18 5 µm, gradient 5%→90% acetonitrile in water+ 0.3% NH₄OH, 120 mL/min).

Yield: 13 mg (12% of theory)

ESI mass spectrum: [M+H]⁺=436

Retention time HPLC: 0.70 min (METHOD A).

The following examples are prepared as described for Example 2.1, employing the corresponding amines, respectively.

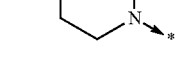

| Example | R¹R²N— | Yield (%) | Formula | MS | Retention time HPLC in min (method) |
|---|---|---|---|---|---|
| 2.2 | 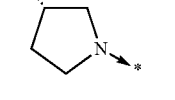 | 15 | C26H28FN3O3 | 450 [M+H]⁺ | 1.78 (A) |
| 2.3 |  | 10 | C26H28FN3O4 | 466 [M+H]⁺ | 1.46 (A) |
| 2.4 |  | 11 | C25H26FN3O4 | 452 [M+H]⁺ | 1.44 (A) |
| 2.5 | \N—* | 7 | C23H24FN3O3 | 410 [M+H]⁺ | 1.56 (A) |
| 2.6 | H-N(Et)-* | 15 | C23H24FN3O3 | 410 [M+H]⁺ | 1.10 (B) |

Example 3.1

4-(5-Chloro-pyridin-2-ylmethoxy)-1-{2-[4-(4-ethyl-piperazin-1-ylmethyl)-2-methyl-phenyl]-2-oxo-ethyl}-1H-pyridin-2-one

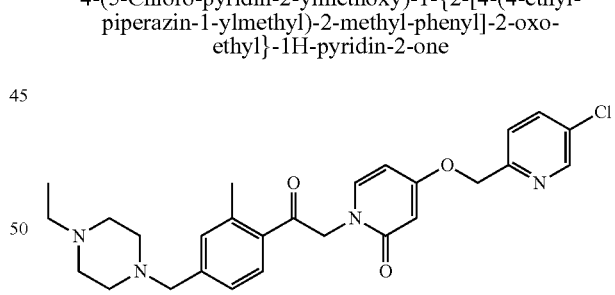

To a solution of 1-[2-(4-bromomethyl-2-methyl-phenyl)-2-oxo-ethyl]-4-(5-chloro-pyridin-2-ylmethoxy)-1H-pyridin-2-one (preparation 3b, 110 mg, 0.23 mmol) in N,N-dimethylacetamide (2 mL) is added Cs₂CO₃ (184 mg, 0.57 mmol) and N-ethylpiperazine (63 µL, 0.75 mmol). The reaction mixture is stirred overnight at room temperature. The mixture is purified via reverse phase HPLC chromatography (Gilson Xbridge C18 5 µm, gradient 5%→90% acetonitrile in water+ 0.3% NH₄OH, 120 mL/min).

Yield: 60 mg (54% of theory)

ESI mass spectrum: [M+H]⁺=495

Retention time HPLC: 1.70 min (METHOD A).

The following examples are prepared as described for Example 3.1, employing the corresponding amines, respectively.

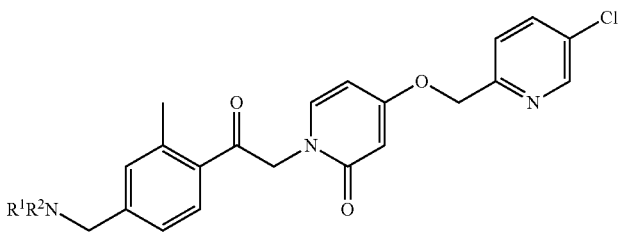
| Example | R¹R²N— | Yield (%) | Formula | MS | Retention time HPLC in min (method) | DSC (melting point) |
|---|---|---|---|---|---|---|
| 3.2 | HO-CH2-pyrrolidinyl | 56 | C26H28ClN3O4 | 482 [M + H]⁺ | 1.67 (A) | |
| 3.3 | 3-HO-pyrrolidinyl | 52 | C25H26ClN3O4 | 468 [M + H]⁺ | 1.57 (A) | |
| 3.4 | 3-HO-pyrrolidinyl | 52 | C25H26ClN3O4 | 468 [M + H]⁺ | 1.57 (A) | |
| 3.5 | 4-methylpiperazinyl | 36 | C26H29ClN4O3 | 481 [M + H]⁺ | 1.60 (A) | |
| 3.6 | piperidinyl | 48 | C26H28ClN3O3 | 466 [M + H]⁺ | 1.92 (A) | |
| 3.7 | 4-HO-piperidinyl | 42 | C26H28ClN3O4 | 482 [M + H]⁺ | 1.58 (A) | |
| 3.8 | pyrrolidinyl | 48 | C25H26ClN3O3 | 452 [M + H]⁺ | 1.82 (A) | |
| 3.9 | N(CH3)2 | 46 | C23H24ClN3O3 | 426 [M + H]⁺ | 1.70 (A) | Onset: 136° C. |
| 3.10 | NHCH3 | 42 | C22H22ClN3O3 | 412 [M + H]⁺ | 1.64 (A) | |
| 3.11 | NHEt | 48 | C23H24ClN3O3 | 426 [M + H]⁺ | 1.71 (A) | |

-continued

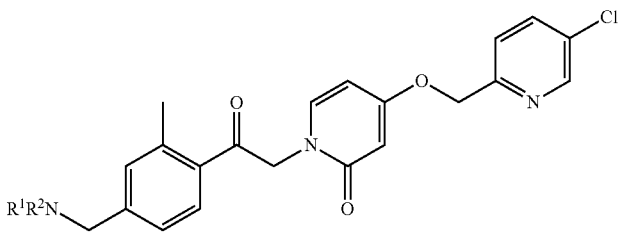

| Example | R¹R²N— | Yield (%) | Formula | MS | Retention time HPLC in min (method) | DSC (melting point) |
|---|---|---|---|---|---|---|
| 3.12 | 4-(hydroxymethyl)piperidin-1-yl | 47 | C27H30ClN3O4 | 496 [M + H]⁺ | 1.63 (A) | |
| 3.13 | 3-hydroxypiperidin-1-yl | 16 | C26H28ClN3O4 | 482 [M + H]⁺ | 1.55 (A) | |
| 3.14 | 2-(hydroxymethyl)piperidin-1-yl | 26 | C27H30ClN3O4 | 496 [M + H]⁺ | 1.74 (A) | |
| 3.15 | 3-hydroxyazetidin-1-yl | 34 | C24H24ClN3O4 | 454 [M + H]⁺ | 1.50 (A) | |
| 3.16 | 3-hydroxy-3-azabicyclo[3.1.1] | 35 | C27H28ClN3O4 | 494 [M + H]⁺ | 1.24 (A) | |

Example 4.1

4-(5-Bromo-pyridin-2-ylmethoxy)-1-[2-(4-dimethy-laminomethyl-2-methyl-phenyl)-2-oxo-ethyl]-1H-pyridin-2-one

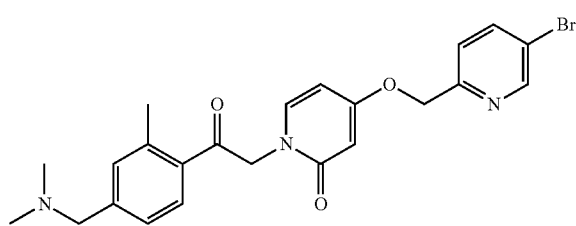 [SMILES: Cc1cc(CN(C)C)ccc1C(=O)Cn1ccc(OCc2ccc(Br)cn2)cc1=O]

To a solution of 1-[2-(4-bromomethyl-2-methyl-phenyl)-2-oxo-ethyl]-4-(5-bromo-pyridin-2-ylmethoxy)-1H-pyridin-2-one (preparation 4b, 1000 mg, 1.98 mmol) in N,N-dimethylacetamide (5 mL) is added dimethylamine (3.0 mL of 2M solution in THF, 6.0 mmol). The reaction mixture is stirred 2 h at room temperature. The mixture is purified via reverse phase HPLC chromatography (Gilson Xbridge C18 5 μm, gradient 5%→90% acetonitrile in water+0.3% NH₄OH, 120 mL/min).

Yield: 300 mg (32% of theory)

ESI mass spectrum: [M+H]⁺=470

Retention time HPLC: 1.68 min (METHOD A).

DSC (melting point): Onset: 136° C.

The following examples are prepared as described for Example 4.1, employing the corresponding amines, respectively.

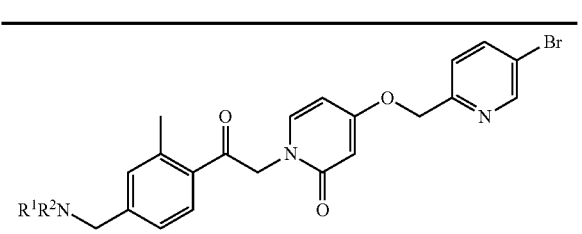

| Example | R¹R²N— | Yield (%) | Formula | MS | Retention time HPLC in min (method) |
|---|---|---|---|---|---|
| 4.2 | HO-piperidin-4-yl | 84 | C26H28BrN3O4 | 526 [M+H]⁺ | 1.56 (A) |
| 4.3 | HOCH2-piperidin-4-yl | 86 | C27H30BrN3O4 | 540 [M+H]⁺ | 1.62 (A) |
| 4.4 | HO-piperidin-3-yl | 70 | C26H28BrN3O4 | 526 [M+H]⁺ | 1.60 (A) |
| 4.5 | HOCH2-pyrrolidin-2-yl | 84 | C26H28BrN3O4 | 526 [M+H]⁺ | 1.64 (A) |
| 4.6 | ethyl-NH- | 67 | C23H24BrN3O3 | 470 [M+H]⁺ | 1.68 (A) |

Example 4.7

(R)-4-(5-Bromo-pyridin-2-ylmethoxy)-1-{2-[4-(2-hydroxymethyl-piperidin-1-ylmethyl)-2-methyl-phenyl]-2-oxo-ethyl}-1H-pyridin-2-one

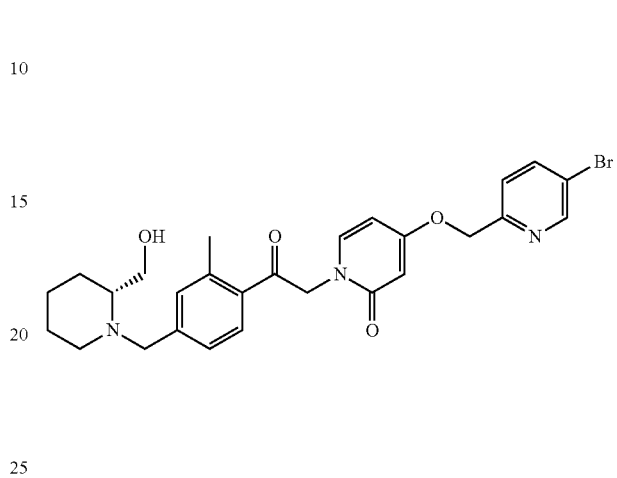

To a solution of 1-[2-(4-bromomethyl-2-methyl-phenyl)-2-oxo-ethyl]-4-(5-bromo-pyridin-2-ylmethoxy)-1H-pyridin-2-one (preparation 4b, 100 mg, 0.20 mmol) in DMF (2 mL) is added (R)-2-hydroxymethylpiperidine hydrochloride (75 mg, 0.50 mmol) and K₂CO₃ (55 mg, 0.40 mmol). The reaction mixture is stirred 2 h at 80° C. The mixture is purified via reverse phase HPLC chromatography (Phenomenex Gemini-C18 10 μm, gradient 5%→90% acetonitrile in water+0.3% NH₄OH, 120 mL/min).

Yield: 22 mg (21% of theory)

ESI mass spectrum: [M+H]⁺=540

Retention time HPLC: 1.69 min (METHOD A).

The following examples are prepared as described for Example 4.7, employing the corresponding amines (as free base), respectively.

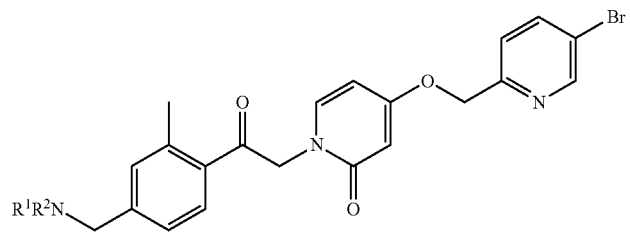

| Example | R¹R²N— | Yield (%) | Formula | MS | Retention time HPLC in min (method) |
|---|---|---|---|---|---|
| 4.8 | pyrrolidin-1-yl | 23 | C25H26BrN3O3 | 496 [M+H]⁺ | 1.75 (A) |

-continued
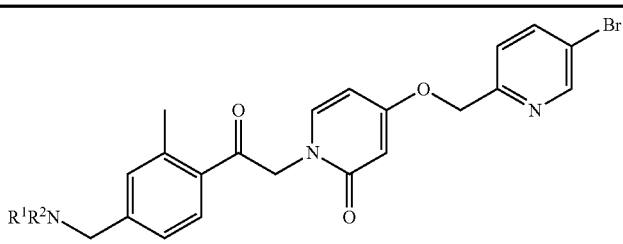
| Example | R¹R²N— | Yield (%) | Formula | MS | Retention time HPLC in min (method) |
|---|---|---|---|---|---|
| 4.9 | (3-hydroxypyrrolidinyl) | 41 | C25H26BrN3O4 | 512 [M + H]⁺ | 1.54 (A) |
| 4.10 | (4-ethylpiperazinyl) | 33 | C27H31BrN4O3 | 539 [M + H]⁺ | 1.64 (A) |
| 4.11 | (morpholinyl) | 30 | C25H26BrN3O4 | 512 [M + H]⁺ | 1.64 (A) |
| 4.12 | (3-hydroxypiperidinyl) | 32 | C26H28BrN3O4 | 526 [M + H]⁺ | 1.64 (A) |
| 4.13 | (methylamino) | 24 | C22H22BrN3O3 | 456 [M + H]⁺ | 1.58 (A) |
| 4.14 | (4-methylpiperazinyl) | 27 | C26H29BrN4O3 | 525 [M + H]⁺ | 1.58 (A) |
| 4.15 | (isopropylamino) | 4 | C24H26BrN3O3 | 484 [M + H]⁺ | 1.70 (A) |

-continued

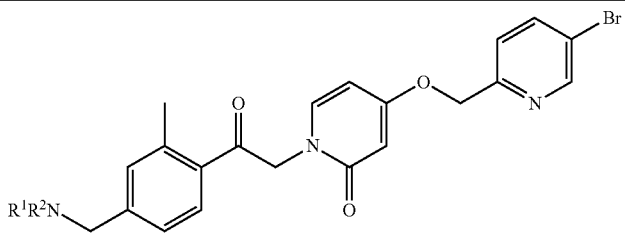

| Example | R¹R²N— | Yield (%) | Formula | MS | Retention time HPLC in min (method) |
|---|---|---|---|---|---|
| 4.16 | piperidin-1-yl | 13 | C26H28BrN3O3 | 510 [M + H]⁺ | 1.86 (A) |
| 4.17 | isopropyl(methyl)amino | 12 | C25H28BrN3O3 | 498 [M + H]⁺ | 1.84 (A) |
| 4.18 | ethyl(methyl)amino | 37 | C24H26BrN3O3 | 484 [M + H]⁺ | 1.74 (A) |
| 4.19 | 2-methylpyrrolidin-1-yl | 15 | C26H28BrN3O3 | 510 [M + H]⁺ | 1.85 (A) |
| 4.20 | diethylamino | 6 | C25H28BrN3O3 | 498 [M + H]⁺ | 1.85 (A) |
| 4.21** | azetidin-1-yl | 43 | C24H24BrN3O3 | 482 [M + H]⁺ | 1.67 (A) |

**preparation according to procedure for example 4.1 employing CH₂Cl₂ as solvent

Example 5.1

(R)-5-Benzyloxy-2-{2-[4-(3-hydroxy-piperidin-1-ylmethyl)-2-methyl-phenyl]-2-oxo-ethyl}-2H-pyridazin-3-one

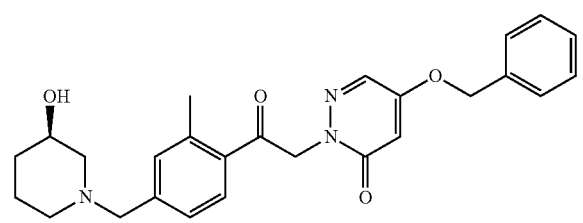 [SMILES: Cc1cc(CN2CCC[C@@H](O)C2)ccc1C(=O)Cn1ncc(OCc2ccccc2)cc1=O]

To a solution of 5-benzyloxy-2-[2-(4-bromomethyl-2-methyl-phenyl)-2-oxo-ethyl]-2H-pyridazin-3-one (preparation 5b, 100 mg, 0.23 mmol) in DMF (2 mL) is added (R)-3-hydroxypiperidine hydrochloride (96 mg, 0.70 mmol) and N-ethyldiisopropylamine (362 µL, 2.1 mmol). The reaction mixture is stirred overnight at room temperature. The mixture is purified via reverse phase HPLC chromatography (Waters Xbridge C18 5 µm, gradient 5%→90% acetonitrile in water+ 0.3% NH₄OH, 120 mL/min).

Yield: 42 mg (40% of theory)

ESI mass spectrum: [M+H]⁺=448

Retention time HPLC: 1.70 min (METHOD A).

The following examples are prepared as described for Example 5.1, employing the corresponding amines (as free base), respectively.

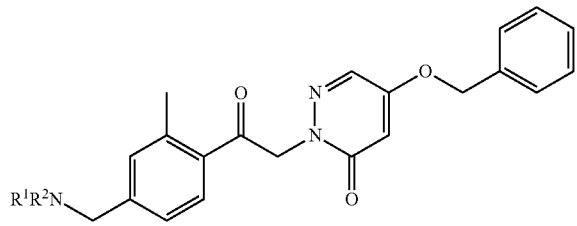
| Example | R¹R²N— | Yield (%) | Formula | MS | Retention time HPLC in min (method) | DSC (melting point) |
|---|---|---|---|---|---|---|
| 5.2 | (CH3)2N—* | 33 | C23H25N3O3 | 392 [M + H]⁺ | 1.78 (A) | Onset: 98° C. |
| 5.3 | (S)-2-(hydroxymethyl)pyrrolidin-1-yl—* | 67 | C26H29N3O4 | 448 [M + H]⁺ | 1.75 (A) | Onset: 109° C. |
| 5.4 | (S)-3-hydroxypyrrolidin-1-yl—* | 54 | C25H27N3O4 | 434 [M + H]⁺ | 1.63 (A) | |
| 5.5 | (R)-3-hydroxypyrrolidin-1-yl—* | 53 | C25H27N3O4 | 434 [M + H]⁺ | 1.63 (A) | |
| 5.6 | EtHN—* | 35 | C23H25N3O3 | 392 [M + H]⁺ | 1.75 (A) | |
| 5.7 | 3-hydroxyazetidin-1-yl—* | 25 | C24H25N3O4 | 420 [M + H]⁺ | 1.58 (A) | |
| 5.8 | 4-hydroxypiperidin-1-yl—* | 38 | C26H29N3O4 | 448 [M + H]⁺ | 1.65 (A) | Onset: 130° C. |
| 5.9 | 2-methylmorpholin-4-yl—* | 67 | C26H29N3O4 | 448 [M + H]⁺ | 1.83 (A) | |

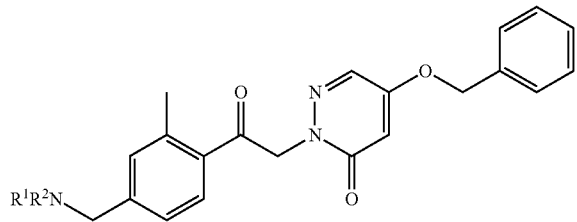

| Example | R¹R²N— | Yield (%) | Formula | MS | Retention time HPLC in min (method) | DSC (melting point) |
|---|---|---|---|---|---|---|
| 5.10 | (2,6-dimethylmorpholin-4-yl) | 70 | C27H31N3O4 | 462 [M + H]⁺ | 1.90 (A) | |
| 5.11 | (4-hydroxymethylpiperidin-1-yl) | 50 | C27H31N3O4 | 462 [M + H]⁺ | 1.71 (A) | |
| 5.12 | (2-hydroxymethylpiperidin-1-yl) | 51 | C27H31N3O4 | 462 [M + H]⁺ | 1.82 (A) | |
| 5.13 | (3-hydroxypiperidin-1-yl) | 45 | C26H29N3O4 | 448 [M + H]⁺ | 1.69 (A) | |
| 5.14 | (3-hydroxy-3-methylpyrrolidin-1-yl) | 58 | C26H29N3O4 | 448 [M + H]⁺ | 1.70 (A) | |

Example 6.1

5-(5-Fluoro-pyridin-2-ylmethoxy)-2-[2-(2-methyl-4-pyrrolidin-1-ylmethyl-phenyl)-2-oxo-ethyl]-2H-pyridazin-3-one

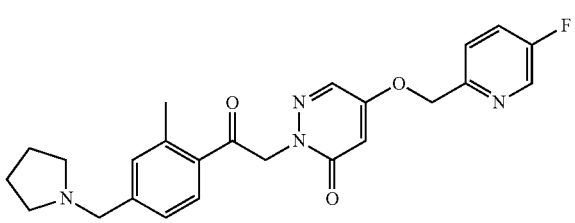 [SMILES: Cc1cc(CN2CCCC2)ccc1C(=O)Cn1ncc(OCc2ccc(F)cn2)cc1=O]

To a solution of 2-[2-(4-bromomethyl-2-methyl-phenyl)-2-oxo-ethyl]-5-(5-fluoro-pyridin-2-ylmethoxy)-2H-pyridazin-3-one (preparation 6b, 112 mg, 0.25 mmol) in DMF (2 mL) is added pyrrolidine (63 µL, 0.75 mmol). The reaction mixture is stirred for 60 min at room temperature. The mixture is purified via reverse phase HPLC chromatography (Gilson Xbridge C18 5 µm, gradient 5%→90% acetonitrile in water+0.3% NH₄OH, 120 mL/min).

Yield: 79 mg (72% of theory)
ESI mass spectrum: [M+H]⁺=437
Retention time HPLC: 1.78 min (METHOD A).

The following examples are prepared as described for Example 6.1, employing the corresponding amines, respectively.

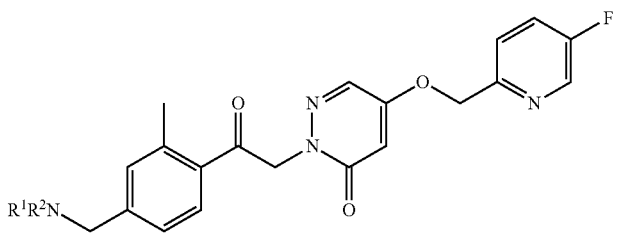

| Example | R¹R²N— | Yield (%) | Formula | MS | Retention time HPLC in min (method) | DSC (melting point) |
|---|---|---|---|---|---|---|
| 6.2 | piperidin-1-yl | 66 | C25H27FN4O3 | 451 [M + H]⁺ | 1.90 (A) | |
| 6.3 | ethylamino | 42 | C22H23FN4O3 | 411 [M + H]⁺ | 1.62 (A) | |
| 6.4 | 4-hydroxypiperidin-1-yl | 59 | C25H27FN4O4 | 467 [M + H]⁺ | 1.52 (A) | |
| 6.5 | dimethylamino | 34 | C22H23FN4O3 | 411 [M + H]⁺ | 1.64 (A) | Onset: 126° C. |
| 6.6 | 3-hydroxypyrrolidin-1-yl | 53 | C24H25FN4O4 | 453 [M + H]⁺ | 1.48 (A) | |

Example 7.1

(S)-5-(5-Chloro-pyridin-2-ylmethoxy)-2-{2-[4-(2-hydroxymethyl-pyrrolidin-1-ylmethyl)-2-methyl-phenyl]-2-oxo-ethyl}-2H-pyridazin-3-one

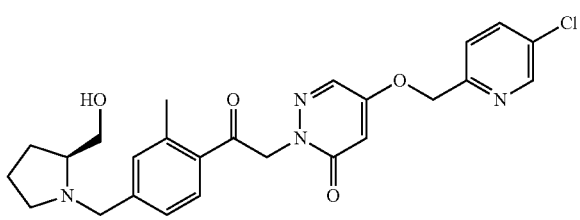 [SMILES: Cc1cc(CN2CCC[C@H]2CO)ccc1C(=O)Cn1ncc(OCc2ccc(Cl)cn2)cc1=O]

To a solution of 2-[2-(4-bromomethyl-2-methyl-phenyl)-2-oxo-ethyl]-5-(5-chloro-pyridin-2-ylmethoxy)-2H-pyridazin-3-one (preparation 7b, 110 mg, 0.24 mmol) in N,N-dimethylacetamide (2 mL) is added Cs₂CO₃ (194 mg, 0.60 mmol) and L-prolinol (37 mg, 0.36 mmol). The reaction mixture is stirred for 2 days at room temperature. The mixture is purified via reverse phase HPLC chromatography (Xbridge C18 5 μm, gradient 5%→90% acetonitrile in water+0.3% NH₄OH, 120 mL/min).

Yield: 81 mg (71% of theory)

ESI mass spectrum: [M+H]⁺=483

Retention time HPLC: 1.04 min (METHOD B).

The following examples are prepared as described for Example 7.1, employing the corresponding amines, respectively.

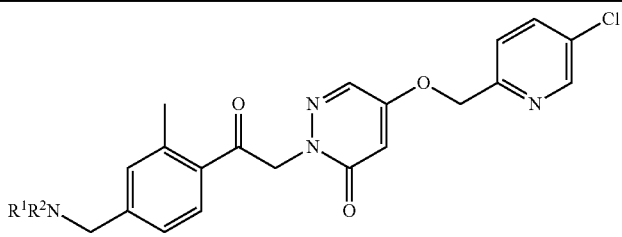

| Example | R¹R²N— | Yield (%) | Formula | MS | Retention time HPLC in min (method) |
|---|---|---|---|---|---|
| 7.2 | (ethyl-piperazinyl) | 60 | C26H30ClN5O3 | 496 [M + H]⁺ | 1.05 (B) |
| 7.3 | 3-hydroxyazetidinyl | 14 | C23H23ClN4O4 | 455 [M + H]⁺ | 1.02 (B) |
| 7.4 | 4-methylpiperazinyl | 49 | C25H28ClN5O3 | 482 [M + H]⁺ | 1.04 (B) |
| 7.5 | piperidinyl | 60 | C25H27ClN4O3 | 467 [M + H]⁺ | 1.08 (B) |
| 7.6 | methylamino | 38 | C21H21ClN4O3 | 413 [M + H]⁺ | 1.02 (B) |
| 7.7 | ethylamino | 46 | C22H23ClN4O3 | 427 [M + H]⁺ | 1.04 (B) |
| 7.8 | 4-(hydroxymethyl)piperidinyl | 61 | C26H29ClN4O4 | 497 [M + H]⁺ | 1.03 (B) |
| 7.9 | (3S)-3-hydroxypyrrolidinyl | 68 | C24H25ClN4O4 | 469 [M + H]⁺ | 1.02 (B) |
| 7.10 | (3S)-3-hydroxypiperidinyl | 58 | C25H27ClN4O4 | 483 [M + H]⁺ | 1.03 (B) |
| 7.11 | (3R)-3-hydroxypiperidinyl | 63 | C25H27ClN4O4 | 483 [M + H]⁺ | 1.03 (B) |

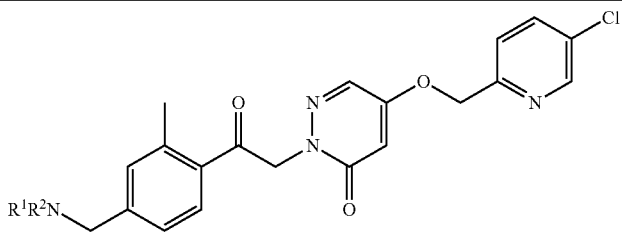

| Example | R¹R²N— | Yield (%) | Formula | MS | Retention time HPLC in min (method) |
|---|---|---|---|---|---|
| 7.12 | HO⟍ ⟨pyrrolidine⟩ N—* | 65 | C24H25ClN4O4 | 469 [M + H]⁺ | 1.02 (B) |
| 7.13 | ⟨piperidine-CH2OH⟩ N—* | 50 | C26H29ClN4O4 | 497 [M + H]⁺ | 1.06 (B) |
| 7.14 | HO⟨piperidine⟩ N—* | 48 | C25H27ClN4O4 | 483 [M + H]⁺ | 1.03 (B) |
| 7.15 | ⟨pyrrolidine⟩ N—* | 50 | C24H25ClN4O3 | 453 [M + H]⁺ | 1.06 (B) |
| 7.16 | (CH3)2N—* | 50 | C22H23ClN4O3 | 427 [M + H]⁺ | 1.03 (B) |

Example 7.17

5-(5-Chloro-pyridin-2-ylmethoxy)-2-[2-(2-methyl-4-piperazin-1-ylmethyl-phenyl)-2-oxo-ethyl]-2H-pyridazin-3-one

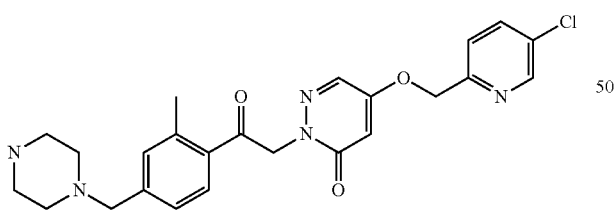

To a solution of 2-[2-(4-bromomethyl-2-methyl-phenyl)-2-oxo-ethyl]-5-(5-chloro-pyridin-2-ylmethoxy)-2H-pyridazin-3-one (preparation 7b, 110 mg, 0.24 mmol) in N,N-dimethylacetamide (2 mL) is added Cs₂CO₃ (194 mg, 0.60 mmol) and Boc-piperazine (65 mg, 0.36 mmol). The reaction mixture is stirred for 2 days at room temperature.

The mixture is purified via reverse phase HPLC chromatography (Xbridge C18 5 μm, gradient 5%→90% acetonitrile in water+0.3% NH₄OH, 120 mL/min) to yield 90 mg of the Boc-protected product (67% of theory). This intermediate is dissolved in CH₂Cl₂ (3 mL), trifluoroacetic acid is added (0.3 mL) and the mixture is stirred overnight at room temperature. The reaction mixture is quenched with aqueous NaHCO₃ solution and extracted with CH₂Cl₂. The organic layer is dried over MgSO₄ and concentrated under reduced pressure.

Yield: 41 mg (55% of theory)
ESI mass spectrum: [M+H]⁺=468
Retention time HPLC: 1.52 min (METHOD A).

Example 8.1

(R)-5-(5-Bromo-pyridin-2-ylmethoxy)-2-{2-[4-(3-hydroxy-pyrrolidin-1-ylmethyl)-2-methyl-phenyl]-2-oxo-ethyl}-2H-pyridazin-3-one

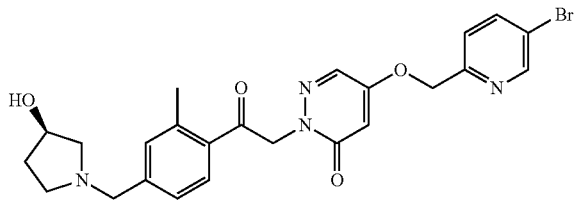 [SMILES: Cc1cc(CN2CC[C@@H](O)C2)ccc1C(=O)Cn1ncc(OCc2ccc(Br)cn2)cc1=O]

To a solution of 2-[2-(4-bromomethyl-2-methyl-phenyl)-2-oxo-ethyl]-5-(5-bromo-pyridin-2-ylmethoxy)-2H-pyridazin-3-one (preparation 8b, 100 mg, 0.20 mmol) in N,N-dimethylacetamide (2 mL) is added Cs$_2$CO$_3$ (160 mg, 0.49 mmol) and (R)-3-hydroxypyrrolidine (22 mg, 0.25 mmol). The reaction mixture is stirred overnight at room temperature. The mixture is purified via reverse phase HPLC chromatography (Phenomenex Gemini-C18 10 μm, gradient 5%→90% acetonitrile in water+0.3% NH$_4$OH, 120 mL/min).

Yield: 78 mg (77% of theory)
ESI mass spectrum: [M+H]$^+$=513
Retention time HPLC: 0.91 min (METHOD D).

The following examples are prepared as described for Example 8.1, employing the corresponding amines, respectively.

| Example | R$^1$R$^2$N— | Yield (%) | Formula | MS | Retention time HPLC in min (method) | DSC (melting point) |
|---|---|---|---|---|---|---|
| 8.2 | HO-azetidinyl | 29 | C23H23BrN4O4 | 499 [M + H]$^+$ | 0.89 (D) | |
| 8.3 | dimethylamino | 68 | C22H23BrN4O3 | 471 [M + H]$^+$ | 0.86 (D) | Onset: 157° C. |
| 8.4 | 3-hydroxypiperidinyl | 76 | C25H27BrN4O4 | 527 [M + H]$^+$ | 0.90 (D) | Onset: 128° C. |
| 8.5 | 3-hydroxy-3-methylpyrrolidinyl | 66 | C25H27BrN4O4 | 527 [M + H]$^+$ | 0.92 (D) | |
| 8.6 | 3-hydroxypiperidinyl | 80 | C25H27BrN4O4 | 527 [M + H]$^+$ | 0.90 (D) | |
| 8.7 | 2-(hydroxymethyl)piperidinyl | 70 | C26H29BrN4O4 | 541 [M + H]$^+$ | 0.93 (D) | |
| 8.8 | ethylamino | 67 | C22H23BrN4O3 | 471 [M + H]$^+$ | 0.92 (D) | |
| 8.9 | 4-hydroxypiperidinyl | 96 | C25H27BrN4O4 | 527 [M + H]$^+$ | 0.90 (D) | Onset: 168° C. |
| 8.10 | methylamino | 59 | C21H21BrN4O3 | 457 [M + H]$^+$ | 0.90 (D) | |

-continued

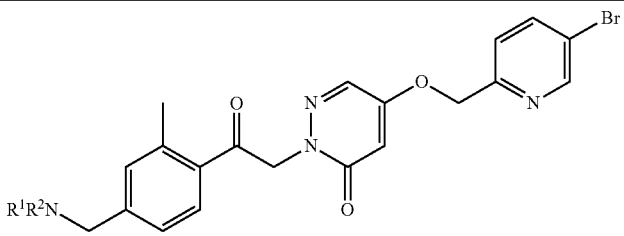

| Example | R¹R²N— | Yield (%) | Formula | MS | Retention time HPLC in min (method) | DSC (melting point) |
|---|---|---|---|---|---|---|
| 8.11 | [pyrrolidinyl-CH₂-OH structure] | 50 | C25H27BrN4O4 | 527 [M + H]⁺ | 0.91 (D) | |

Example 9.1

2-[2-(4-Dimethylaminomethyl-2-methyl-phenyl)-2-oxo-ethyl]-5-(5-methoxy-pyridin-2-ylmethoxy)-2H-pyridazin-3-one

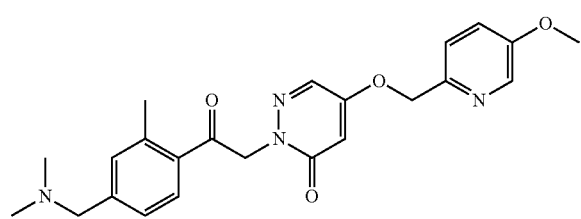

To a solution of 2-[2-(4-Bromomethyl-2-methyl-phenyl)-2-oxo-ethyl]-5-(5-methoxy-pyridin-2-ylmethoxy)-2H-pyridazin-3-one (preparation 9d, 120 mg, 0.26 mmol) in N,N-dimethylacetamide (2 mL) is added dimethylamine (0.76 mmol, 2 M solution in THF). The reaction mixture is stirred for 4 h at 40° C. The mixture is purified via reverse phase HPLC chromatography (Waters XBridge 5 μm, gradient 5%→90% acetonitrile in water+0.3% NH₄OH, 120 mL/min).
Yield: 51 mg (46% of theory)
ESI mass spectrum: [M+H]⁺=423
Retention time HPLC: 1.64 min (METHOD A).
DSC (melting point): Onset: 122° C.

2-[2-(4-Dimethylaminomethyl-2-methyl-phenyl)-2-oxo-ethyl]-5-(5-methoxy-pyridin-2-ylmethoxy)-2H-pyridazin-3-one, monohydrochloride

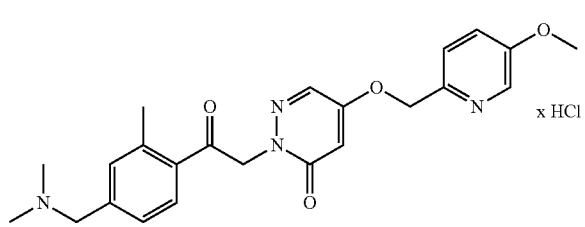

The hydrochloride salt of the compound 9.1 is prepared by adding a 1.1 equivalent of HCl (as 10 M solution of HCl in ethanol) to a concentrated solution of the corresponding free base in refluxing ethanol. The hydrochloride salt, which precipitates upon cooling, is filtered off and dried under reduced pressure.
DSC (melting point): Onset: 212° C.

Example 9.1c

2-[2-(4-Dimethylaminomethyl-phenyl)-2-oxo-ethyl]-5-(5-methoxy-pyridin-2-ylmethoxy)-2H-pyridazin-3-one

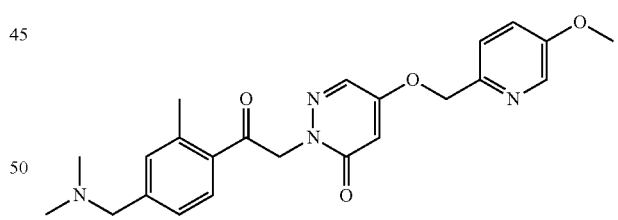

The title compound as comparative example can be prepared from 2-bromo-1-(4-hydroxymethyl-phenyl)-ethanone (preparation described in WO2008/22979) and 5-(5-methoxy-pyridin-2-ylmethoxy)-2H-pyridazin-3-one (preparation 9b) in analogy to the preparation of example 9.1.
ESI mass spectrum: [M+H]⁺=409
Retention time HPLC: 1.01 min (METHOD E).

The following examples are prepared as described for Example 9.1, employing the corresponding amines, respectively.

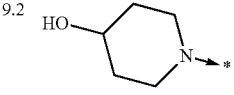

| Example | R¹R²N— | Yield (%) | Formula | MS | Retention time HPLC in min (method) |
|---|---|---|---|---|---|
| 9.2 | 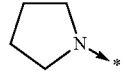 | 36 | C26H30N4O5 | 479 [M + H]⁺ | 1.53 (A) |
| 9.3 |  | 38 | C25H28N4O4 | 449 [M + H]⁺ | 1.75 (A) |
| 9.4 |  | 34 | C22H24N4O4 | 409 [M + H]⁺ | 0.90 (E) |
| 9.5 | 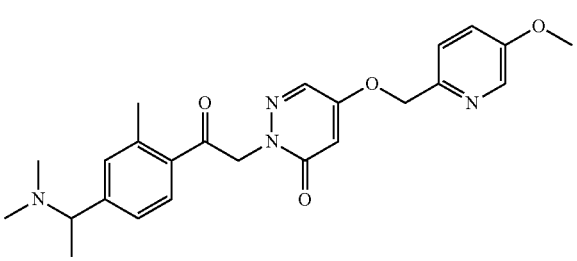 | 54 | C23H26N4O4 | 423 [M + H]⁺ | 1.61 (A) |

Example 10.1

2-{2-[4-(1-Dimethylamino-ethyl)-2-methyl-phenyl]-2-oxo-ethyl}-5-(5-methoxy-pyridin-2-ylmethoxy)-2H-pyridazin-3-one

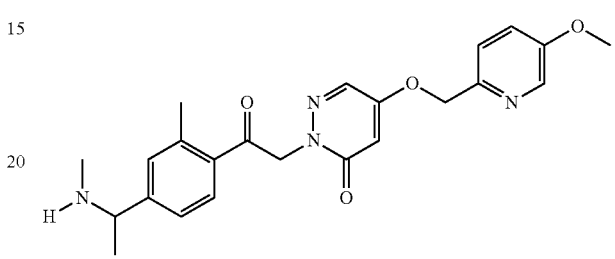

To a solution of 2-{2-[4-(1-Bromo-ethyl)-2-methyl-phenyl]-2-oxo-ethyl}-5-(5-methoxy-pyridin-2-ylmethoxy)-2H-pyridazin-3-one (preparation 10d, 1.55 g, 3.28 mmol) in CH$_2$Cl$_2$ (5 mL) is added a solution of dimethylamine (2 M in THF, 4.9 mL, 9.8 mmol). The reaction mixture is stirred overnight at room temperature. After dilution with CH$_2$Cl$_2$, the mixture is washed with aqueous NaHCO$_3$ solution. The organic layer is dried over MgSO$_4$ and evaporated under reduced pressure. The crude product is purified via reverse phase HPLC chromatography (Phenomenex Gemini C18, gradient 30%→95% methanol in water+0.1% NH$_4$OH, 120 mL/min).

Yield: 293 mg (21% of theory)

ESI mass spectrum: [M+H]⁺=437

Retention time HPLC: 1.48 min (METHOD C)

Example 10.2

5-(5-Methoxy-pyridin-2-ylmethoxy)-2-{2-[2-methyl-4-(1-methylamino-ethyl)-phenyl]-2-oxo-ethyl}-2H-pyridazin-3-one

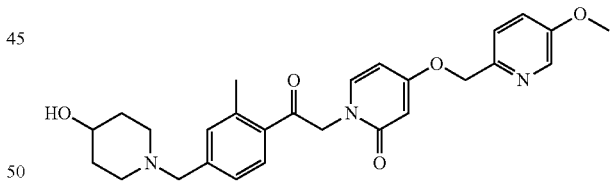

5-(5-Methoxy-pyridin-2-ylmethoxy)-2-{2-[2-methyl-4-(1-methylamino-ethyl)-phenyl]-2-oxo-ethyl}-2H-pyridazin-3-one is prepared following the procedure for example 10.1, employing methylamine instead of dimethylamine.

Yield: 25% of theory

ESI mass spectrum: [M+H]⁺=423

Retention time HPLC: 1.41 min (METHOD C).

Example 11.1

1-{2-[4-(4-Hydroxy-piperidin-1-ylmethyl)-2-methyl-phenyl]-2-oxo-ethyl}-4-(5-methoxy-pyridin-2-yl-methoxy)-1H-pyridin-2-one To a mixture of 1-[2-(4-bromomethyl-2-methyl-phenyl)-2-oxo-ethyl]-4-(5-methoxy-pyridin-2-ylmethoxy)-1H-pyridin-2-one (preparation 11d, 129 mg, 0.28 mmol) in CH$_2$Cl$_2$ (2 mL) is added 4-hydroxypiperidine (85 mg, 0.84 mmol). The reaction mixture is stirred overnight at room temperature. The mixture is purified via reverse phase HPLC chromatography (Waters Xbridge C18 5 µm, gradient 50%→95% methanol in water+0.1% NH$_4$OH, 120 mL/min).

Yield: 25 mg (18% of theory)

ESI mass spectrum: [M+H]⁺=478

Retention time HPLC: 0.95 min (METHOD E).

The following examples are prepared as described for Example 11.1, employing the corresponding amines, respectively.

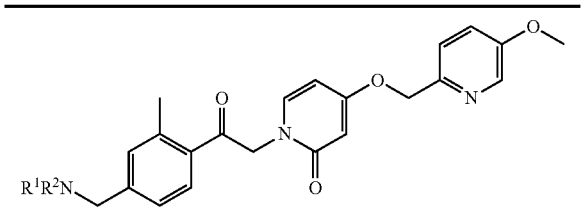

| Example | R¹R²N— | Yield (%) | Formula | MS | Retention time HPLC in min (method) |
|---|---|---|---|---|---|
| 11.2 | (dimethylamino-methyl) | 9 | C24H27N3O4 | 422 [M + H]⁺ | 0.98 (E) |
| 11.3 | (pyrrolidinyl-methyl) | 31 | C26H29N3O4 | 448 [M + H]⁺ | 1.05 (E) |
| 11.4 | (ethylamino-methyl) | 34 | C24H27N3O4 | 422 [M + H]⁺ | 0.95 (E) |

Some test methods for determining an MCH-receptor antagonistic activity will now be described. In addition, other test methods known to the skilled man may be used, e.g. by inhibiting the MCH-receptor-mediated inhibition of cAMP production, as described by Hoogduijn M et al. in "Melanin-concentrating hormone and its receptor are expressed and functional in human skin", Biochem. Biophys. Res Commun. 296 (2002) 698-701 and by biosensory measurement of the binding of MCH to the MCH receptor in the presence of antagonistic substances by plasmon resonance, as described by Karlsson O P and Lofas S. in "Flow-Mediated On-Surface Reconstitution of G-Protein Coupled Receptors for Applications in Surface Plasmon Resonance Biosensors", Anal. Biochem. 300 (2002), 132-138. Other methods of testing antagonistic activity to MCH receptors are contained in the references and patent documents mentioned hereinbefore, and the description of the test methods used is hereby incorporated in this application.

MCH-1 Receptor Binding Test
Method: MCH binding to hMCH-1R transfected cells
Species: Human
Test cell: hMCH-1R stably transfected into CHO/Galpha16 cells
Results: IC50 values Membranes from CHO/Galpha16 cells stably transfected with human hMCH-1R are resuspended using a syringe (needle 0.6×25 mm) and diluted in test buffer (50 mM HEPES, 10 mM $MgCl_2$, 2 mM EGTA, pH 7.00; 0.1% bovine serum albumin (protease-free), 0.021% bacitracin, 1 μg/ml aprotinin, 1 μg/ml leupeptin and 1 μM phosphoramidone) to a concentration of 5 to 15 μg/ml. 200 microliters of this membrane fraction (contains 1 to 3 μg of protein) are incubated for 60 minutes at ambient temperature with 100 pM of $^{125}$I-tyrosyl melanin concentrating hormone ($^{125}$I-MCH commercially obtainable from NEN) and increasing concentrations of the test compound in a final volume of 250 microliters. After the incubation the reaction is filtered using a cell harvester through 0.5% PEI treated fibreglass filters (GF/B, Unifilter Packard). The membrane-bound radioactivity retained on the filter is then determined after the addition of scintillator substance (Packard Microscint 20) in a measuring device (TopCount of Packard).

The non-specific binding is defined as bound radioactivity in the presence of 1 micromolar MCH during the incubation period.

The analysis of the concentration binding curve is carried out on the assumption of one receptor binding site.
Standard:
Non-labelled MCH competes with labelled $^{125}$I-MCH for the receptor binding with an
IC50 value of between 0.06 and 0.15 nM.
The KD value of the radioligand is 0.156 nM.

The compounds according to the invention typically have $IC_{50}$ values in the range from about 1 nM to about 200 nM, preferably from 1 nM to 50 nM. In order to illustrate that compounds according to the invention with different structural elements possess a very good MCH-1 receptor antagonistic activity, the $IC_{50}$ values of the compounds depicted in the following table are provided.

| Example No. | $IC_{50}$ [nM] |
|---|---|
| 1.1 | 20 |
| 1.2 | 19 |
| 1.3 | 19 |
| 1.4 | 40 |
| 1.5 | 48 |
| 1.6 | 24 |
| 1.7 | 11 |
| 1.8 | 17 |
| 1.9 | 11 |
| 1.10 | 26 |
| 1.11 | 30 |
| 1.12 | 21 |
| 1.13 | 29 |
| 1.14 | 53 |
| 1.15 | 31 |
| 1.16 | 29 |
| 1.17 | 26 |
| 1.18 | 16 |
| 2.1 | 67 |
| 2.2 | 116 |
| 2.3 | 93 |
| 2.4 | 70 |
| 2.5 | 70 |
| 2.6 | 134 |
| 3.1 | 79 |
| 3.2 | 36 |
| 3.3 | 39 |
| 3.4 | 38 |
| 3.5 | 84 |
| 3.6 | 26 |
| 3.7 | 36 |
| 3.8 | 26 |
| 3.9 | 32 |
| 3.10 | 37 |
| 3.11 | 26 |
| 3.12 | 34 |
| 3.13 | 34 |
| 3.14 | 37 |
| 3.15 | 31 |
| 3.16 | 19 |
| 4.1 | 17 |

-continued

| Example No. | IC$_{50}$ [nM] |
|---|---|
| 4.2 | 16 |
| 4.3 | 13 |
| 4.4 | 18 |
| 4.5 | 13 |
| 4.6 | 50 |
| 4.7 | 14 |
| 4.8 | 17 |
| 4.9 | 20 |
| 4.10 | 53 |
| 4.11 | 59 |
| 4.12 | 23 |
| 4.13 | 26 |
| 4.14 | 72 |
| 4.15 | 18 |
| 4.16 | 12 |
| 4.17 | 18 |
| 4.18 | 19 |
| 4.19 | 14 |
| 4.20 | 19 |
| 4.21 | 18 |
| 5.1 | 14 |
| 5.2 | 9 |
| 5.3 | 11 |
| 5.4 | 12 |
| 5.5 | 11 |
| 5.6 | 10 |
| 5.7 | 10 |
| 5.8 | 15 |
| 5.9 | 30 |
| 5.10 | 35 |
| 5.11 | 13 |
| 5.12 | 13 |
| 5.13 | 13 |
| 5.14 | 10 |
| 6.1 | 38 |
| 6.2 | 35 |
| 6.3 | 59 |
| 6.4 | 58 |
| 6.5 | 50 |
| 6.6 | 49 |
| 7.1 | 26 |
| 7.2 | 71 |
| 7.3 | 27 |
| 7.4 | 67 |
| 7.5 | 16 |
| 7.6 | 28 |
| 7.7 | 18 |
| 7.8 | 26 |
| 7.9 | 32 |
| 7.10 | 25 |
| 7.11 | 31 |
| 7.12 | 30 |
| 7.13 | 35 |
| 7.14 | 30 |
| 7.15 | 19 |
| 7.16 | 24 |
| 7.17 | 83 |
| 8.1 | 22 |
| 8.2 | 19 |
| 8.3 | 16 |
| 8.4 | 24 |
| 8.5 | 18 |
| 8.6 | 21 |
| 8.7 | 20 |
| 8.8 | 17 |
| 8.9 | 18 |
| 8.10 | 25 |
| 8.11 | 21 |
| 9.1 | 28 |
| 9.2 | 34 |
| 9.3 | 25 |
| 9.4 | 20 |
| 9.5 | 24 |
| 10.1 | 20 |
| 10.2 | 22 |
| 11.1 | 53 |

-continued

| Example No. | IC$_{50}$ [nM] |
|---|---|
| 11.2 | 57 |
| 11.3 | 26 |
| 11.4 | 54 |

Determination of Metabolic Degradation in Human Hepatocytes for Compounds of the Invention The metabolic degradation of the test compound is determined in a hepatocyte suspension. Hepatocytes (typically cryopreserved) are incubated in an appropriate buffer system (e.g. Dulbecco's modified eagle medium plus 3.5 μg glucagon/500 mL, 2.5 mg insulin/500 mL and 3.75 mg/500 mL hydrocortison) containing 5% human serum.

Following a (typically) 30 min preincubation in an incubator (37° C., 10% $CO_2$), 5 μl of test compound solution (80 μM; from 2 mM in DMSO stock solution diluted 1:25 with medium) are added into 395 μl hepatocyte suspension (cell density in the range 0.25-5 Mio cells/mL, typically 1 Mio cells/mL; final concentration of test compound 1 μM, final DMSO concentration 0.05%). The cells are incubated for six hours (incubator, orbital shaker) and samples (25 μl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

Decline of parent compound is analyzed by HPLC-MS/MS.

CLint is calculated as follows CL_INTRINSIC=Dose/AUC=(CO/CD)/(AUD+clast/k)×1000/60. C0: initial concentration in the incubation [μM], CD: cell density of vital cells [10e6 cells/mL], AUD: area under the data [μM×h], clast: concentration of last data point [μM], k: slope of the regression line for parent decline [h−1].

The calculated in vitro hepatic intrinsic clearance can be scaled up to the intrinsic in vivo hepatic clearance and used to predict hepatic in vivo blood clearance (CL) by the use of a liver model (well stirred model).

CL_INTRINSIC_INVIVO [ml/min/kg]=(CL_INTRINSIC [μL/min/10e6 cells]×hepatocellularity [10e6 cells/g liver]×liver factor [g/kg bodyweight])/1000

CL [ml/min/kg]=CL_INTRINSIC_INVIVO [ml/min/kg]×hepatic blood flow [ml/min/kg]/(CL_INTRINSIC_INVIVO [ml/min/kg]+hepatic blood flow [ml/min/kg])

Hepatocellularity, human: 120×10e6 cells/g liver

Liver factor, human: 25.7 g liver/kg bodyweight

Hepatic blood flow, human: 21 ml/(min×kg)

In the following table the intrinsic clearance CLint is provided for compounds according to this invention with a methyl substituent in ortho-position of the central phenyl ring in comparison with corresponding compounds without said methyl substitution.

| Structure | | CLint [μL/min/10e6 cells] |
|---|---|---|
| Example 4.1 in this application | [Structure: 4-((5-bromopyridin-2-yl)methoxy)-1-(2-(4-((dimethylamino)methyl)-2-methylphenyl)-2-oxoethyl)pyridin-2(1H)-one] | 20.7 |
| Example 11.2 in WO2009/103478 | [Structure: 4-((5-bromopyridin-2-yl)methoxy)-1-(2-(4-((dimethylamino)methyl)phenyl)-2-oxoethyl)pyridin-2(1H)-one] | 66.1 |
| Example 6.5 in this application | [Structure: 5-((5-fluoropyridin-2-yl)methoxy)-2-(2-(4-((dimethylamino)methyl)-2-methylphenyl)-2-oxoethyl)pyridazin-3(2H)-one] | 1.7 |
| Example 33.5 in WO2008/22979 | [Structure: 5-((5-fluoropyridin-2-yl)methoxy)-2-(2-(4-((dimethylamino)methyl)phenyl)-2-oxoethyl)pyridazin-3(2H)-one] | 10.0 |
| Example 8.3 in this application | [Structure: 5-((5-bromopyridin-2-yl)methoxy)-2-(2-(4-((dimethylamino)methyl)-2-methylphenyl)-2-oxoethyl)pyridazin-3(2H)-one] | 11.5 |
| Example 12.2 in WO2009/103478 | [Structure: 5-((5-bromopyridin-2-yl)methoxy)-2-(2-(4-((dimethylamino)methyl)phenyl)-2-oxoethyl)pyridazin-3(2H)-one] | 57.6 |

-continued

| Structure | CLint [μL/min/10e6 cells] |
|---|---|
| Example 5.2 in this application | 4.8 |
| Example 32.7 in WO2008/22979 | 16.8 |
| Example 1.8 in this application | 3.9 |
| Example 29.8 in WO2008/22979 | 24.3 |
| Example 3.9 in this application | 13.8 |
| Example 9.2 in WO2009/103478 | 68.8 |

| Structure | CLint [μL/min/10e6 cells] |
|---|---|
| Example 9.1 in this application | 3.3 |
| Example 9.1c in this application | 27 |

From the above comparative data it can be well seen that the compounds according to this invention show a much lower intrinsic clearance than the comparative compounds without a ortho-methyl-substitution and thus compounds according to the invention are metabolically more stable.

Pharmacological Example

The following example shows the effect on body weight development of a compound according to this invention. All experimental protocols concerning the use of laboratory animals are reviewed by a federal Ethics Committee and approved by governmental authorities. The time course of body weight is followed over a treatment period of 8 days in female diet-induced obese Wistar rats (RjHan:Wi) with a mean body weight of about 340 g at the start of the study. In addition to a normal rodent diet, the rats had received a daily changing diet admixture consisting of palatable commercially available supermarket foods (like chocolate bars). From day 1 to day 8, the animals (n=6/group) receive two daily oral administrations of either vehicle alone (0.5% aqueous hydroxyethylcellulose, 0.015% polysorbat 80) or the test compound dissolved in this vehicle. Body weight is measured daily before the second administration. The data are presented as mean±S.E.M. of baseline-corrected body weight change. Statistical comparison is conducted by repeated measures two-way ANOVA followed by Bonferroni post tests for group-wise comparisons. A p value <0.05 is considered to show a statistically significant difference. Control animals are dosed twice daily with vehicle. Animals are dosed with vehicle in the morning and 3, 10, or 30 mg/kg of the compound in the evening (once daily compound dosing; qd). Body weight reduction is observed at least in the groups with higher dosing. Animals which receive 3 or 10 mg/kg of compound in the morning and evening (twice daily dosing; bid) show a higher body weight loss versus control.

What is claimed is:
1. A compound of formula I

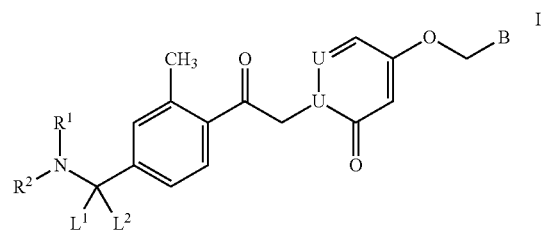

wherein
$R^1$, $R^2$ independently of each other are selected from the group consisting of H, $C_{1-6}$-alkyl and $C_{3-7}$-cycloalkyl, while the alkyl or cycloalkyl group may be mono- or polysubstituted by identical or different groups $R^{11}$, and a —$CH_2$— group in position 3 or 4 of a 5-, 6- or 7-membered cycloalkyl group may be replaced by —O—, —S—, —S(=O)—, —S(=O)$_2$— or —$NR^{12}$—; or
$R^1$ and $R^2$ are linked to each other and together form a group which is selected from the group consisting of a $C_{3-6}$-alkylene bridge, wherein a —$CH_2$— group not adjacent to the N atom of the $R^1R^2N$— group may be replaced by —O—, —S—, —S(=O)—, —S(=O)$_2$— or —$NR^{12}$—, and wherein one or more H atoms of the alkylene bridge may be replaced by identical or different groups $R^{11}$; or
$R^1$ and $R^2$ are linked to each other such that the $R^1R^2N$— group forms a bridged cyclic ring system with 5 to 8 C-atoms wherein one or more H atoms of the bridged cyclic ring system may be replaced by identical or different groups $R^{11}$; and
$L^1$, $L^2$ independently of each other are selected from the group consisting of H and $C_{1-3}$-alkyl, or $L^1$ and $L^2$ are linked to each other and together form a group which is selected from the group consisting of a $C_{2-5}$-alkylene bridge; and U is selected from the group consisting of CH and N; and B is selected from the group consisting of phenyl and pyridinyl each of which may be mono- or polysubstituted by identical or different substituents $R^{20}$; and $R^{11}$ is selected from the group consisting of OH, F, Cl, Br, CN, $C_{1-6}$-alkyl, $C_{3-6}$-cycloalkyl, $C_{1-4}$-alkyl-O— and $R^{13}R^{14}N$—, while each of the above mentioned alkyl or cycloalkyl groups may be substituted independently of one another by one or more substituents selected from F, Cl, Br, OH, CN, $CF_3$, $C_{1-3}$-alkyl, $C_{1-3}$-alkyl-O— and HO—$C_{1-3}$-alkyl; and $R^{12}$ is selected from the group consisting of H, $C_{1-4}$-alkyl and $C_{1-4}$-alkyl-C(=O)—; and $R^{13}$, $R^{14}$ independently of each other are selected from the group consisting of H and $C_{1-4}$-alkyl; and $R^{20}$ is selected from the group consisting of F, Cl, Br, OH, CN, $NO_2$, $C_{1-4}$-alkyl and $C_{1-4}$-alkyl-O—, wherein each alkyl group may be substituted with one or more substituents independently of each other selected from F, Cl, Br, OH, CN, $NO_2$ and $C_{1-4}$-alkyl-O—; and while, unless otherwise stated, the above-mentioned alkyl groups may be straight-chain or branched, or a pharmaceutically acceptable salt thereof.

2. The compound according to claim 1 wherein $R^1$ and $R^2$ independently of each other are selected from the group consisting of H, $C_{1-4}$-alkyl and $C_{3-6}$-cycloalkyl, while the alkyl or cycloalkyl group may be mono- or polysubstituted by identical or different groups $R^{11}$, and a —$CH_2$— group in position 3 or 4 of a 5- or 6-membered cycloalkyl group may be replaced by —O— or —$NR^{12}$—, or the groups $R^1$ and $R^2$ are linked to each other and together form a group which is selected from the group consisting of a $C_{3-5}$-alkylene bridge, wherein a —$CH_2$— group not adjacent to the N atom of the $R^1R^2N$— group may be replaced by —O— or —$NR^{12}$—, and wherein 1 or 2 H atoms of the alkylene bridge may be replaced by identical or different groups $R^{11}$, wherein $R^{11}$ and $R^{12}$ are defined as in claim 1, or a pharmaceutically acceptable salt thereof.

3. The compound according to claim 1 wherein the groups $L^1$ and $L^2$ are independently of each other selected from the group consisting of H and $CH_3$, or a pharmaceutically acceptable salt thereof.

4. The compound according to claim 1 wherein the group U denotes CH.

5. The compound according to claim 1 wherein the group U denotes N, or a pharmaceutically acceptable salt thereof.

6. The compound according to claim 1 wherein the compound is selected from the group of formulas I.1.1, I.1.2, I.2.1 and I.2.2

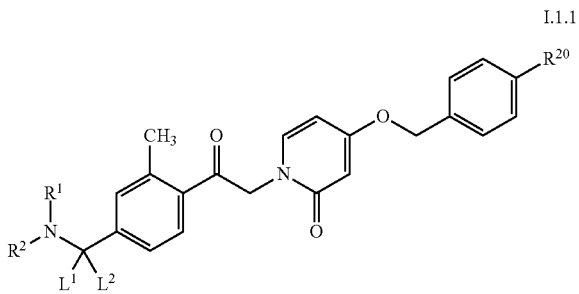

I.1.1

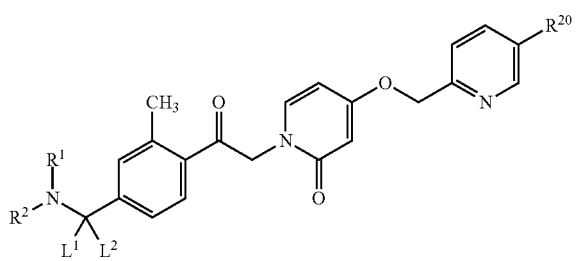

I.1.2

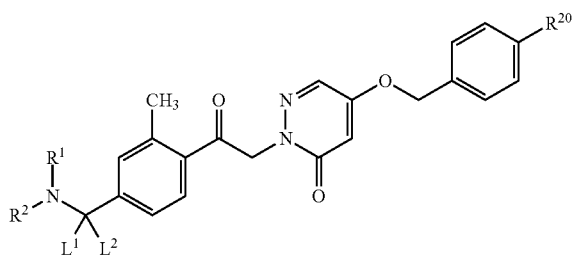

I.2.1

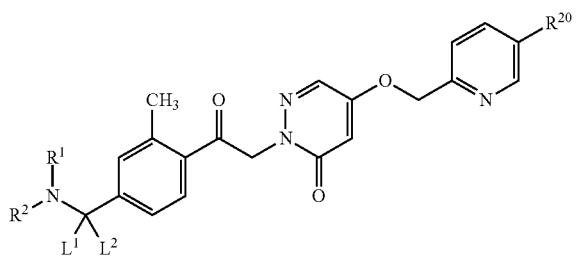

I.2.2 or a pharmaceutically acceptable salt thereof.

7. The compound according to claim 1 selected from the group of compounds

| | |
|---|---|
| 1.1 | 4-Benzyloxy-1-{2-[4-(3-hydroxy-azetidin-1-ylmethyl)-2-methyl-phenyl]-2-oxo-ethyl}-1H-pyridin-2-one |
| 1.2 | 4-Benzyloxy-1-[2-(2-methyl-4-methylaminomethyl-phenyl)-2-oxo-ethyl]-1H-pyridin-2-one |
| 1.3 | 4-Benzyloxy-1-{2-[4-(4-hydroxy-piperidin-1-ylmethyl)-2-methyl-phenyl]-2-oxo-ethyl}-1H-pyridin-2-one |
| 1.5 | 4-Benzyloxy-1-{2-[2-methyl-4-(4-methyl-piperazin-1-ylmethyl)-phenyl]-2-oxo-ethyl}-1H-pyridin-2-one |
| 1.6 | 4-Benzyloxy-1-{2-[4-(4-hydroxymethyl-piperidin-1-ylmethyl)-2-methyl-phenyl]-2-oxo-ethyl}-1H-pyridin-2-one |
| 1.7 | 4-Benzyloxy-1-[2-(2-methyl-4-pyrrolidin-1-ylmethyl-phenyl)-2-oxo-ethyl]-1H-pyridin-2-one |
| 1.8 | 4-Benzyloxy-1-[2-(4-dimethylaminomethyl-2-methyl-phenyl)-2-oxo-ethyl]-1H-pyridin-2-one |
| 1.11 | (S)-4-Benzyloxy-1-{2-[4-(3-hydroxy-pyrrolidin-1-ylmethyl)-2-methyl-phenyl]-2-oxo-ethyl}-1H-pyridin-2-one |
| 1.12 | 4-Benzyloxy-1-[2-(4-ethylaminomethyl-2-methyl-phenyl)-2-oxo-ethyl]-1H-pyridin-2-one |
| 1.13 | (S)-4-Benzyloxy-1-{2-[4-(3-hydroxy-piperidin-1-ylmethyl)-2-methyl-phenyl]-2-oxo-ethyl}-1H-pyridin-2-one |
| 1.15 | (R)-4-Benzyloxy-1-{2-[4-(3-hydroxy-piperidin-1-ylmethyl)-2-methyl-phenyl]-2-oxo-ethyl}-1H-pyridin-2-one |
| 1.17 | (S)-4-Benzyloxy-1-{2-[4-(2-hydroxymethyl-pyrrolidin-1-ylmethyl)-2-methyl-phenyl]-2-oxo-ethyl}-1H-pyridin-2-one |
| 3.2 | 4-(5-Chloro-pyridin-2-ylmethoxy)-1-{2-[4-((S)-2-hydroxymethyl-pyrrolidin-1-ylmethyl)-2-methyl-phenyl]-2-oxo-ethyl}-1H-pyridin-2-one |
| 3.4 | (R)-4-(5-Chloro-pyridin-2-ylmethoxy)-1-{2-[4-(3-hydroxy-pyrrolidin-1-ylmethyl)-2-methyl-phenyl]-2-oxo-ethyl}-1H-pyridin-2-one |
| 3.8 | 4-(5-Chloro-pyridin-2-ylmethoxy)-1-[2-(2-methyl-4-pyrrolidin-1-ylmethyl-phenyl)-2-oxo-ethyl]-1H-pyridin-2-one |

| | |
|---|---|
| 3.9 | 4-(5-Chloro-pyridin-2-ylmethoxy)-1-[2-(4-dimethylaminomethyl-2-methyl-phenyl)-2-oxo-ethyl]-1H-pyridin-2-one |
| 3.11 | 4-(5-Chloro-pyridin-2-ylmethoxy)-1-[2-(4-ethylaminomethyl-2-methyl-phenyl)-2-oxo-ethyl]-1H-pyridin-2-one |
| 3.13 | (R)-4-(5-Chloro-pyridin-2-ylmethoxy)-1-{2-[4-(3-hydroxy-piperidin-1-ylmethyl)-2-methyl-phenyl]-2-oxo-ethyl}-1H-pyridin-2-one |
| 3.15 | 4-(5-Chloro-pyridin-2-ylmethoxy)-1-{2-[4-(3-hydroxy-azetidin-1-ylmethyl)-2-methyl-phenyl]-2-oxo-ethyl}-1H-pyridin-2-one |
| 4.1 | 4-(5-Bromo-pyridin-2-ylmethoxy)-1-[2-(4-dimethylaminomethyl-2-methyl-phenyl)-2-oxo-ethyl]-1H-pyridin-2-one |
| 4.2 | 4-(5-Bromo-pyridin-2-ylmethoxy)-1-{2-[4-(4-hydroxy-piperidin-1-ylmethyl)-2-methyl-phenyl]-2-oxo-ethyl}-1H-pyridin-2-one |
| 4.3 | 4-(5-Bromo-pyridin-2-ylmethoxy)-1-{2-[4-(4-hydroxymethyl-piperidin-1-ylmethyl)-2-methyl-phenyl]-2-oxo-ethyl}-1H-pyridin-2-one |
| 4.4 | (S)-4-(5-Bromo-pyridin-2-ylmethoxy)-1-{2-[4-(3-hydroxy-piperidin-1-ylmethyl)-2-methyl-phenyl]-2-oxo-ethyl}-1H-pyridin-2-one |
| 4.5 | (S)-4-(5-Bromo-pyridin-2-ylmethoxy)-1-{2-[4-(2-hydroxymethyl-pyrrolidin-1-ylmethyl)-2-methyl-phenyl]-2-oxo-ethyl}-1H-pyridin-2-one |
| 4.6 | 4-(5-Bromo-pyridin-2-ylmethoxy)-1-[2-(4-ethylaminomethyl-2-methyl-phenyl)-2-oxo-ethyl]-1H-pyridin-2-one |
| 4.8 | 4-(5-Bromo-pyridin-2-ylmethoxy)-1-[2-(2-methyl-4-pyrrolidin-1-ylmethyl-phenyl)-2-oxo-ethyl]-1H-pyridin-2-one |
| 4.9 | (R)-4-(5-Bromo-pyridin-2-ylmethoxy)-1-{2-[4-(3-hydroxy-pyrrolidin-1-ylmethyl)-2-methyl-phenyl]-2-oxo-ethyl}-1H-pyridin-2-one |
| 4.12 | (R)-4-(5-Bromo-pyridin-2-ylmethoxy)-1-{2-[4-(3-hydroxy-piperidin-1-ylmethyl)-2-methyl-phenyl]-2-oxo-ethyl}-1H-pyridin-2-one |
| 4.13 | 4-(5-Bromo-pyridin-2-ylmethoxy)-1-[2-(2-methyl-4-methylaminomethyl-phenyl)-2-oxo-ethyl]-1H-pyridin-2-one |
| 4.15 | 4-(5-Bromo-pyridin-2-ylmethoxy)-1-{2-[4-(isopropylamino-methyl)-2-methyl-phenyl]-2-oxo-ethyl}-1H-pyridin-2-one |
| 4.17 | 4-(5-Bromo-pyridin-2-ylmethoxy)-1-(2-{4-[(isopropyl-methyl-amino)-methyl]-2-methyl-phenyl}-2-oxo-ethyl)-1H-pyridin-2-one |
| 4.18 | 4-(5-Bromo-pyridin-2-ylmethoxy)-1-(2-{4-[(ethyl-methyl-amino)-methyl]-2-methyl-phenyl}-2-oxo-ethyl)-1H-pyridin-2-one |
| 4.20 | 4-(5-Bromo-pyridin-2-ylmethoxy)-1-[2-(4-diethylaminomethyl-2-methyl-phenyl)-2-oxo-ethyl]-1H-pyridin-2-one |
| 4.21 | 1-[2-(4-Azetidin-1-ylmethyl-2-methyl-phenyl)-2-oxo-ethyl]-4-(5-bromo-pyridin-2-ylmethoxy)-1H-pyridin-2-one |
| 5.2 | 5-Benzyloxy-2-[2-(4-dimethylaminomethyl-2-methyl-phenyl)-2-oxo-ethyl]-2H-pyridazin-3-one |
| 5.3 | (S)-5-Benzyloxy-2-{2-[4-(2-hydroxymethyl-pyrrolidin-1-ylmethyl)-2-methyl-phenyl]-2-oxo-ethyl}-2H-pyridazin-3-one |
| 5.4 | (R)-5-Benzyloxy-2-{2-[4-(3-hydroxy-pyrrolidin-1-ylmethyl)-2-methyl-phenyl]-2-oxo-ethyl}-2H-pyridazin-3-one |
| 5.6 | 5-Benzyloxy-2-[2-(4-ethylaminomethyl-2-methyl-phenyl)-2-oxo-ethyl]-2H-pyridazin-3-one |
| 5.7 | 5-Benzyloxy-2-{2-[4-(3-hydroxy-azetidin-1-ylmethyl)-2-methyl-phenyl]-2-oxo-ethyl}-2H-pyridazin-3-one |
| 5.9 | 5-Benzyloxy-2-{2-[2-methyl-4-(2-methyl-morpholin-4-ylmethyl)-phenyl]-2-oxo-ethyl}-2H-pyridazin-3-one |
| 5.11 | 5-Benzyloxy-2-{2-[4-(4-hydroxymethyl-piperidin-1-ylmethyl)-2-methyl-phenyl]-2-oxo-ethyl}-2H-pyridazin-3-one |
| 5.12 | (R)-5-Benzyloxy-2-{2-[4-(2-hydroxymethyl-piperidin-1-ylmethyl)-2-methyl-phenyl]-2-oxo-ethyl}-2H-pyridazin-3-one |
| 5.13 | (S)-5-Benzyloxy-2-{2-[4-(3-hydroxy-piperidin-1-ylmethyl)-2-methyl-phenyl]-2-oxo-ethyl}-2H-pyridazin-3-one |
| 5.14 | 5-Benzyloxy-2-{2-[4-(3-hydroxy-3-methyl-pyrrolidin-1-ylmethyl)-2-methyl-phenyl]-2-oxo-ethyl}-2H-pyridazin-3-one |
| 6.1 | 5-(5-Fluoro-pyridin-2-ylmethoxy)-2-[2-(2-methyl-4-pyrrolidin-1-ylmethyl-phenyl)-2-oxo-ethyl]-2H-pyridazin-3-one |
| 6.2 | 5-(5-Fluoro-pyridin-2-ylmethoxy)-2-[2-(2-methyl-4-piperidin-1-ylmethyl-phenyl)-2-oxo-ethyl]-2H-pyridazin-3-one |
| 7.1 | (S)-5-(5-Chloro-pyridin-2-ylmethoxy)-2-{2-[4-(2-hydroxymethyl-pyrrolidin-1-ylmethyl)-2-methyl-phenyl]-2-oxo-ethyl}-2H-pyridazin-3-one |
| 7.6 | 5-(5-Chloro-pyridin-2-ylmethoxy)-2-[2-(2-methyl-4-methylaminomethyl-phenyl)-2-oxo-ethyl]-2H-pyridazin-3-one |
| 7.7 | 5-(5-Chloro-pyridin-2-ylmethoxy)-2-[2-(4-ethylaminomethyl-2-methyl-phenyl)-2-oxo-ethyl]-2H-pyridazin-3-one |
| 7.13 | (R)-5-(5-Chloro-pyridin-2-ylmethoxy)-2-{2-[4-(2-hydroxymethyl-piperidin-1-ylmethyl)-2-methyl-phenyl]-2-oxo-ethyl}-2H-pyridazin-3-one |
| 7.14 | 5-(5-Chloro-pyridin-2-ylmethoxy)-2-{2-[4-(4-hydroxy-piperidin-1-ylmethyl)-2-methyl-phenyl]-2-oxo-ethyl}-2H-pyridazin-3-one |
| 7.15 | 5-(5-Chloro-pyridin-2-ylmethoxy)-2-[2-(2-methyl-4-pyrrolidin-1-ylmethyl-phenyl)-2-oxo-ethyl]-2H-pyridazin-3-one |
| 7.16 | 5-(5-Chloro-pyridin-2-ylmethoxy)-2-[2-(4-dimethylaminomethyl-2-methyl-phenyl)-2-oxo-ethyl]-2H-pyridazin-3-one |
| 8.2 | 5-(5-Bromo-pyridin-2-ylmethoxy)-2-{2-[4-(3-hydroxy-azetidin-1-ylmethyl)-2-methyl-phenyl]-2-oxo-ethyl}-2H-pyridazin-3-one |
| 8.3 | 5-(5-Bromo-pyridin-2-ylmethoxy)-2-[2-(4-dimethylaminomethyl-2-methyl-phenyl)-2-oxo-ethyl]-2H-pyridazin-3-one |
| 8.6 | (R)-5-(5-Bromo-pyridin-2-ylmethoxy)-2-{2-[4-(3-hydroxy-piperidin-1-ylmethyl)-2-methyl-phenyl]-2-oxo-ethyl}-2H-pyridazin-3-one |
| 8.7 | (R)-5-(5-Bromo-pyridin-2-ylmethoxy)-2-{2-[4-(2-hydroxymethyl-piperidin-1-ylmethyl)-2-methyl-phenyl]-2-oxo-ethyl}-2H-pyridazin-3-one |
| 8.8 | 5-(5-Bromo-pyridin-2-ylmethoxy)-2-[2-(4-ethylaminomethyl-2-methyl-phenyl)-2-oxo-ethyl]-2H-pyridazin-3-one |
| 8.9 | 5-(5-Bromo-pyridin-2-ylmethoxy)-2-{2-[4-(4-hydroxy-piperidin-1-ylmethyl)-2-methyl-phenyl]-2-oxo-ethyl}-2H-pyridazin-3-one |
| 8.10 | 5-(5-Bromo-pyridin-2-ylmethoxy)-2-[2-(2-methyl-4-methylaminomethyl-phenyl)-2-oxo-ethyl]-2H-pyridazin-3-one |
| 9.1 | 2-[2-(4-Dimethylaminomethyl-2-methyl-phenyl)-2-oxo-ethyl]-5-(5-methoxy-pyridin-2-ylmethoxy)-2H-pyridazin-3-one |
| 9.2 | 2-{2-[4-(4-Hydroxy-piperidin-1-ylmethyl)-2-methyl-phenyl]-2-oxo-ethyl}-5-(5-methoxy-pyridin-2-ylmethoxy)-2H-pyridazin-3-one |
| 9.3 | 5-(5-Methoxy-pyridin-2-ylmethoxy)-2-[2-(2-methyl-4-pyrrolidin-1-ylmethyl-phenyl)-2-oxo-ethyl]-2H-pyridazin-3-one |
| 9.4 | 5-(5-Methoxy-pyridin-2-ylmethoxy)-2-[2-(2-methyl-4-methylaminomethyl-phenyl)-2-oxo-ethyl]-2H-pyridazin-3-one |
| 9.5 | 2-[2-(4-Ethylaminomethyl-2-methyl-phenyl)-2-oxo-ethyl]-5-(5-methoxy-pyridin-2-ylmethoxy)-2H-pyridazin-3-one |
| 10.1 | 2-{2-[4-(1-Dimethylamino-ethyl)-2-methyl-phenyl]-2-oxo-ethyl}-5-(5-methoxy-pyridin-2-ylmethoxy)-2H-pyridazin-3-one |
| 10.2 | 5-(5-Methoxy-pyridin-2-ylmethoxy)-2-{2-[2-methyl-4-(1-methylamino-ethyl)-phenyl]-2-oxo-ethyl}-2H-pyridazin-3-one | or a pharmaceutically acceptable salt thereof.

8. The pharmaceutically acceptable salt of a compound according to claim 1.

9. A pharmaceutical composition comprising one or more compounds according to claim 1 or one or more pharmaceutically acceptable salts thereof, optionally together with one or more excipients.

10. A method for treating obesity in a patient in need thereof characterized in that a compound according to claim 1 or a pharmaceutically acceptable salt thereof is administered to the patient.

11. A method for reducing food consumption in an obese patient in need thereof characterized in that a compound according to claim 1 or a pharmaceutically acceptable salt thereof is administered to the patient.

* * * * *